United States Patent [19]

Berman et al.

[11] Patent Number: 4,855,224

[45] Date of Patent: Aug. 8, 1989

[54] MOLECULARLY CLONED DIAGNOSTIC PRODUCT AND METHOD OF USE

[75] Inventors: Phillip W. Berman; Laurence A. Lasky, both of San Francisco, Calif.

[73] Assignee: Genentech, Inc., South San Francisco, Calif.

[21] Appl. No.: 776,059

[22] Filed: Sep. 13, 1985

Related U.S. Application Data

[63] Continuation of Ser. No. 587,763, Mar. 9, 1984, abandoned, which is a continuation-in-part of Ser. No. 527,916, Aug. 30, 1983, abandoned, and a continuation-in-part of Ser. No. 547,552, Oct. 31, 1983, abandoned.

[51] Int. Cl.$^4$ .................. C12Q 1/70; C12N 15/00; C12N 5/00
[52] U.S. Cl. ..................... 435/5; 435/172.3; 435/68; 435/240.2; 435/70
[58] Field of Search ............ 435/68, 172.3, 240.2, 435/91, 7, 5; 935/12, 27, 32, 34, 70, 71

[56] References Cited

U.S. PATENT DOCUMENTS

| | | | |
|---|---|---|---|
| 4,315,907 | 2/1982 | Fridlender et al. | 435/7 |
| 4,336,336 | 6/1982 | Silhavy et al. | 435/172.3 |
| 4,399,216 | 8/1983 | Axel et al. | 435/317 |
| 4,442,205 | 4/1984 | Hamer et al. | 435/317 |
| 4,618,578 | 10/1986 | Burke et al. | 435/172.3 |
| 4,642,333 | 2/1987 | Person | 530/350 |

FOREIGN PATENT DOCUMENTS

| | | | |
|---|---|---|---|
| 2079288 | 1/1982 | United Kingdom | 935/12 |
| 2105344 | 3/1983 | United Kingdom | 935/12 |

OTHER PUBLICATIONS

Wisdom, Clinical Chemistry 22(8) pp. 1243–1255 (1976).
Watson et al., Science 218, pp. 381–384 (1982).
Middleton et al., Journal of Virology 43(3), pp. 1091–1101 (1982).
Rose et al., Cell 30, pp. 753–762 (1982).
Lee et al., Journal of Virology 43(1), pp. 41–49 (1982).
Kaufman et al., Molecular and Cellular Biology 2(11), pp. 1304–1319 (1982).
Watson et al., Nucleic Acids Research 11(5), pp. 1507–1522 (1983).
Lee et al., Proc. Natl. Acad. Sci. 79, pp. 6612–6616 (1982).
Frink et al., Journal of Virology 45(2), pp. 634–647 (1983).

*Primary Examiner*—Charles F. Warren
*Assistant Examiner*—Jasemine C. Chambers
*Attorney, Agent, or Firm*—Walter H. Dreger

[57] ABSTRACT

A molecularly cloned diagnostic product in the form of a polypeptide with antigenic determinants capable of specifically binding complementary antibody, the polypeptide being expressed from a stable continuous cell line. With a glycoprotein D of Herpes Simplex Virus (HSV) as the polypeptide, HSV antibody in a specimen is detected in an immunological procedure. With a glycoprotein C fragment from HSV type 2, HSV type 2 may be distinguished from HSV type 1.

34 Claims, 28 Drawing Sheets

Fig. 1A (Part 1)

```
                          *  ***    *  *******   *   *******  * *
HSV2 gD Gene   AGAGCGGTGGGGGGGGGGGAAGAAACTAAAAACACATCAAGCCCACAACCCTCCACAAGGGGTTATGGC
HSV1 gD Gene                                       CCCCGGCCCCAACAAAATCACGGT

*  **  *** *   ****        ********  **      *   *  *    **
HSV2 gD Gene   GGACCCACC--GCACCACCATACTCCGATTCGACCACCATATGCAACCAAATCACCCCCAGAGGGAAGTTCCAT
HSV1 gD Gene   AGCCCG

Fig. 1A (Part 2)

Fig. 1A (Part 3)

```
                                  *                         *                         *                         *
HSV2 gD Gene     451  GTCTGCCCCATCCGAACGCAGCCCCGCTGGAGCTACTATGACAGCTTTAGGCGCCGTCAGCGGAGGATAAACCTGGGA
HSV1 gD Gene          GCCTGTCCCATCCGAACGCAGCCCCGCTGGAACTACTATGACAGCTTCAGCGCCGTCAGCGGAGGATAAACCTGGGG
HSV2 gD Protein  151  Val CysProIleArgThrGlnProArgTrpSerTyrTyrAspSerPheSerAlaValSerGlyArgIleAsnLeuGly
HSV1 gD Protein       Ala CysProIleArgThrGlnProArgTrpAsnTyrTyrAspSerPheSerAlaValSerGlyArgIleAsnLeuGly

*                         *                         *                         *
HSV2 gD Gene     526  TTCCTGATGCACGCCCCCGCCTTCGAGACCGCCTACGTACCTGCGGCTACCTGCGGCTAGTGAAGATAAACGACTGGACGGAG
HSV1 gD Gene          TTCCTGATGCACGCCCCCGCCTTTGAGACCGCCTTTGAGACCGCCTACGTACCTGCGGCTACCTGCGGCTGAAGATAAACGACTGGACGGAG
HSV2 gD Protein  176  PheLeuMetHisAlaProAlaPheGluThrAlaGlyThrAlaGlyThrAlaGlyLeuValLysIleAsnAspTrpThrGlu
HSV1 gD Protein       PheLeuMetHisAlaProAlaPheGluThrAlaGlyThrAlaGlyLeuValLysIleAsnAspTrpThrGlu

*                      *  *                         *                         *
HSV2 gD Gene     601  ATCACACAATTTATCCTGGAGCACCGGGCCCCGCCTCTCCCCGCTGCGCATCCCCCGGCA
HSV1 gD Gene          ATTACACAGTTTATCCTGGAGCACCGAGCCAAGGGCCTCCTGTAAGTACACACCCTCCCGCGTCA
HSV2 gD Protein  201  IleThrGlnP

Fig. 1B (Part 1)

```
                  *              *              *              *              *              *
HSV2 gD Gene   826 ACCCTGCTGCCGCCGGAGCTGTCCGACACCACCACCAACGCCACGACCCCGAACCCGAACTCGTTCCGGAAGACCCCGAGGAC
HSV1 gD Gene       ACCCTGCTGCCGCCGG

Fig. 1B (Part 2)

```
                                      *                  *   ******  *  *****
HSV2 gD Gene     1126  CGTCTCCCCCACATCCGGATGACGACGACGCGCCCCCTCGCACCAGCCATTGTTTACTAGAGGAGTTTCCCGCT
HSV1 gD Gene           CGCCTCCCCCACATCCGGAAGACGACGACCAGCCGTCCTCGCACCAGCCCTTGTTTTTACTAGA----TACCCC---
HSV2 gD Protein   376  ArgLeuProHisIleArg[AspAspAsp]ProProSerHisGlnProLeuPheTyrSTOP
HSV1 gD Protein        ArgLeuProHisIleArg[GluAspAsp]ProSerSerHisGlnProLeuPheTyrSTOP

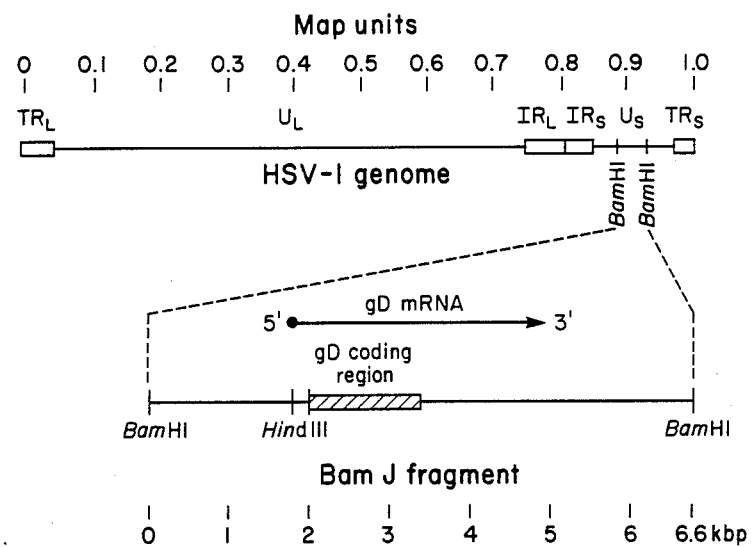
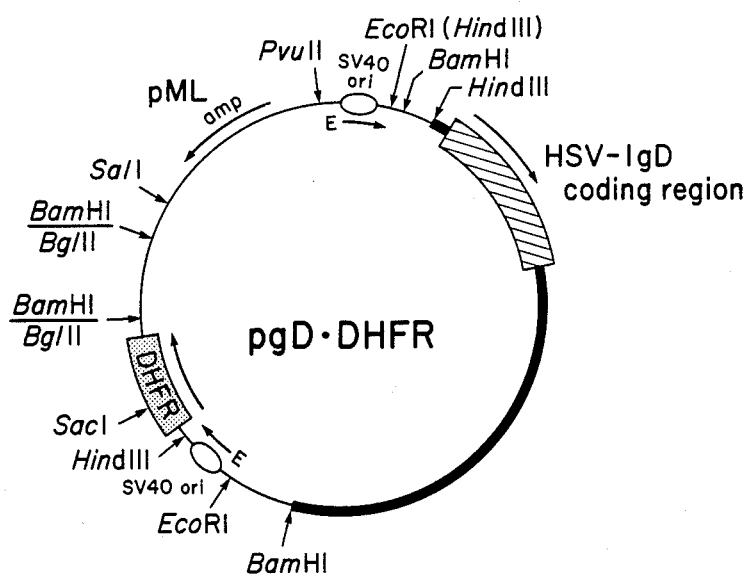
Fig. 3.
1. Digest with HindIII and BamHI
2. Isolate 4.6 kb gD encoding fragment
3. Ligate into HindIII-BamHI cleaved DHFR vector

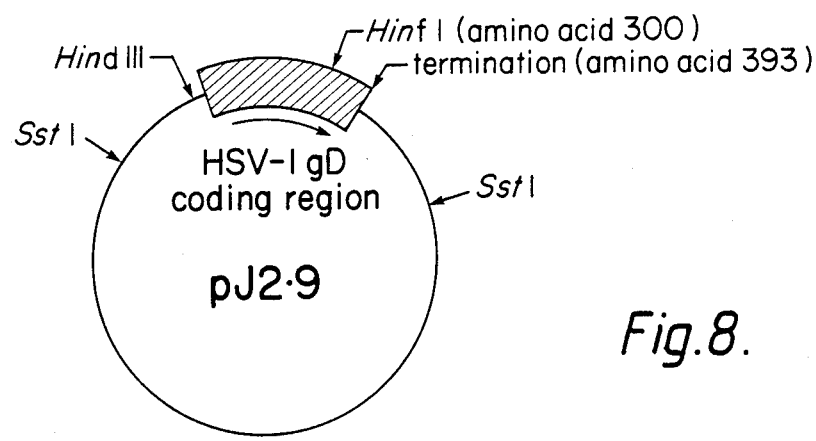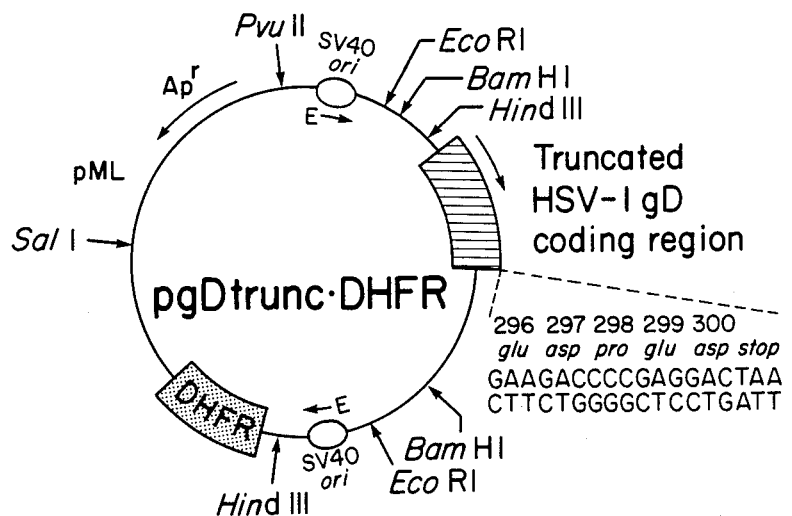
Fig. 8.

Fig.13(Part 1)

```
              *  ***  *      **    *  ***    **    *     **      *       ****               *
HSV-1   G-GATGGGGCCCGGGTATAAATTCCGGAAGGGACACGGGCTACCCTCACTACCGAGGGC        60
HSV-2   GTGCCGTGGA-CGGGTATAAAGGCCAGGGGGGCAGGCGGGGC--CCATCACTGTT-AGGGT
                 "TATA 1"                                  -----> HSV-1 gC
                                                          mRNA 5' end

*  *      ***  **     *     *    *     *   *    ***    *  **
HSV-1   GCTTGGTCGGGAGGCCGCATCGAACGC-ACACCCCATCCGGTGG---TC--CGTGTGGA       120
HSV-2   GTTAGGTTGGGAGGTGGCACAAAAAGCGACACACACCCGTGTTGTTGTCGGGGAGGC

*    *******       *       **       **      ***   ***    **
HSV-1   GGTCGTTTTCAGTGCCCGTC-TCGCTTTGCCGGGAACGCTAGCCGATCCCTCGCAAGG       180
HSV-2   GGTGGTTTCCGGCAACCC--TCCTCGCTGCGCCGGGGCGCCCACCGGTCCTTCGGGGGG

***  ******  **         *          *              **          *
HSV-1   GGGAGGCG---TCGGG-CATGGCCCCCTGGGCGGGGTGGGCCTTGCCGTGTCCTGTGGGC       240
HSV-2   GCCGGGGCTCTTCTGGTCATGGCCCTTGGACGGGTGGGCCTAACCGTGGGCCTGTGGGGC
                      HSV-1 gC, HSV-2 gF initiation codons

*      **       ****    *  ***********
HSV-1   CTGTTGTGGCTCGGGGCTCGGGGCGGGGGTGGCCGGGGGCTCGGAAACTGCCTCCACGGGCCCACG       300
HSV-2   CTGCTGTGGGTGGGTGGGTGTGGTCGTCGTGGTGCTGGCCAAT------GCCTCCCCCGGACGCACG

*    *      *     *     **            *        *************
HSV-1   ATCACCGCGGGAGCGGTGACGAACGCGAGCGAGCCCCACATCGGGGTCCCCCGGGTCA       360
HSV-2   ATAACGGTGGGCCCGCGGGGAACGCGGAGCGGAGCAATGCCGCGCCCCCTCG---------
```

Fig.13 (Part 2)

```
             ************************************************
HSV-1  GCCGCCAGCCCGGAAGTCACCCCACATGACCCCAAACCCCAACAATGTCACACAAAAC   420
HSV-2  ------------------------------------------------------------
       ********  **** ***         **       *        *
HSV-1  AAAACCACCCCCACCGAGCCGGCCAGCCCCCAACAACCCCAAGCCCCACCTCCACGCCC   480
HSV-2  ------GTCCCCGGAACGATCCGCCCCCGAACCACGCCCACACCGCCCCCCAACCCCGC
       ***** **** *******      *  **  ****** *******       ***
HSV-1  AAAAGCCCCCCCACGTCCACCCCCGACCCCAAACCCCGACCCCAAGAACAACACCCCAAG   540
HSV-2  AAGGCGACGAAAAGTAAGGCCTCCACCGCCCAAACGGCCCGCCCC------CCC----AAG
       * * ****** *    * * ** *** ***                *
HSV-1  TCGGGCCGCCCCACTAAACCCCCGGG---CCCGTGTGGTGCGACCGCCGCGACCCATTG   600
HSV-2  ACCGGG---CCCCGAAGACATCCTCGGAGCCCGTGCCGTGCAACCGCCACGACCCGCTG
       * *  *****      *                *    **     *         *
HSV-1  GCCCGGTACGGCTCGCGGGTGCAGATCCGATGCCGGTTTCGGAATTCCACCCGCATGGAG   660
HSV-2  GCCCGGTACGGCTCGCGGGTGCAAATCCGATGCCGGTTTCCCAACTCCACCCGCACGGAG
               *                              *    *** *     *
HSV-1  TTCCGCCTCCAGATATGGCGTTACTCCATGGGTCCGTCCCCCAATCGCTCCGGCTCCC    720
HSV-2  TCCGCCTCCAGATCTGGCGTTATGCCACGGCCGACGGCCGAGATCGGAACGGCGCCT
       **  *  *** ***   ** **    *** * ***        *
HSV-1  GACCTAGAGGAGGTCCTGACGAACATCACCGCCCCACCCGGGGGACTCCTGGTGTACGAC  780
HSV-2  AGCTTAGAGGAGGTGATGGTAAACGTGTCGGCCCCGCCCGGCGGGGCCAACTGGTGTATGAC
```

Fig.13(Part 3)

```
                                                                                         *
HSV-1  AGCGCCCCCAACCTGACGGACCCCCACGTGCTCTGGGCGGAGGGGCCGGCCCCGGGCGCC    840
HSV-2  AGCGCCCCCAACCGAACGGACCCGACGTCGGGCGGGGAGGGGCCGCCGGCCCCGGGCGCC
        **           **     *  **   **  *          *     **
HSV-1  GACCCTCCGTTGTATTCTGTCACCGGGCCGCTGCCGACCCAGCGGCTGATTATCGGCGAG    900
HSV-2  AGCCCGCGGCTGTACTCGGTCGTCGTCGGGCCGCTGGGCCAGCGGCTCATCATCGAAGAG
        *  ****  *   **    **  **  **          **        **     **
HSV-1  GTGACGCCCCGCGACCCAGGGAATGTATTACTTGGCCTGGGGCCGGATGGACAGCCCGCAC    960
HSV-2  CTGACCTTGGAGACCCAGGGCCATGTACTACTGGGTGTGGGGCCGACCGGACCGCCCGTCC
        *      *     *     *  *    *  **  *  **   **        **
HSV-1  GAGTACGGGGACGTGGGGTGCGCGTCCGGCATGTTCCCGCCCCCCGTCTCTGACCCTCCAGCCC    1020
HSV-2  GCGTACGGGGACCTGGGCGTGGTCGCGTTCGCGTGTTCCGCCCTCCGTTCCGTCGCTGACCATCCACCCC
                                      *
HSV-1  CACGCGGTGATGGAGGGTCAGCCGTTCAAGGCGACGTGCACGGCCGCGCCTACTACCCG    1080
HSV-2  CACGGGGTGCTGGAGGGCCAGCCAGTCGTTTAAGGCGACGCCGCCGCCACCTACTACCCG
        *  *    *    *        *         *   **   **
HSV-1  CGTAACCCCGTGGAGTTTGACTGGTTCGAGGACGACCGCCAGGTGTTTAACCCGGGCCAG    1140
HSV-2  GGCAACCGCGCGGGAGTTCGTCGTCGTCGGTTCGAGGACGGTCGCCGGGTATTCGATCCGGCCCAG
        **                                *                *
HSV-1  ATCGACACGCAGACGCCACGAGCACCCCGACGGGTTCACCACAGTCTCTACCGTGACCTCC    1200
HSV-2  ATACACACGCAGACGCAGGAGAACCCCGACGCGGCTTTTCCACCGTCCACCGTGACCTCC
                                           *
HSV-1  GAGGCTGTCGGCGGCCAGGTCCCCCGGGACCTTCACCTGCCAGATGACGTGGCATCGC    1260
HSV-2  GCGGCCGTCGGCGGCCAGGGCCCCCCCGGCACCTTCACCTGCCACCTGCCAGCTGACGTGGCACCGC
```

Fig.13(Part 4)

```
HSV-1  GACTCCGTGACGTTCTCGCGACGCAATGCCACCGGGCTGGCCTGGTGCTGCCGCGGCCA   1320
HSV-2  GACTCCGTGTCGTTCTCTCGGGCGGCCAACGCCAGCGACGGCACGGCATCGGTGCTGCCGCGGCCA

HSV-1  ACCATCACCACCATGGAATTTGGGGTCCGGCATGTGGTCTGCACGGGCCGGCTGCGTCCCCGAG   1380
HSV-2  ACCATTACCACCATGGAGTTTACGGGCGACCATGCGGTCTGCACGGGCCGGCTGTGCCCGAG

HSV-1  GGCGTGACGTTTGCCTGGTTCCTGGGGACGACCCCTCACCGGGCGGCTAAGTCGGCCGTT   1440
HSV-2  GGGGTGACGTTTGCCTGGTTCCTGGTTCCTGGGGGACGACTCCTCCGCCGGGAGAAGGTGGCCGTC

HSV-1  ACGGCCCAGGAGTCGTGCGACCACCCCGGGCTGGCTACGGTCCGGTCCACCCTGCCCATT   1500
HSV-2  GCGTCCCAGACATCGTGCGGGCGCCCCACGCGCCACGATCCGCTCCACCCCTGCCGGTC

HSV-1  TCGTACGACTACAGCGAGTACATCTGCTGGTTGACCGGATATCCGGCCCGGGATTCCCGTT   1560
HSV-2  TCGTACGACAGCGAGTACATCTGCCGGCGCTGCGGGGGATACCCGGACGGAATTCCGGTC

HSV-1  CTAGAGCACCACCGGCAGTCACCAGCCCCACCCAGGGACCCCCACCGAGCGGCAGGTGATC   1620
HSV-2  CTAGAGCACCACCGGCAGCCACCAGCCCCCGCGGGACCCCCACCGAGCGGCAGGTGATC

HSV-1  GAGGCGATCGAGTGGGTGGGGATTGGAATCGGGGTTCTCGCGGCGGGGGTCCTGGTCGTA   1680
HSV-2  CGGGCGGTGGAGGGGGCGGGGATCGGAGTGGCTGTCTCCTTGTCGCGGTTCTGGCCCGGG
```

Fig.13(Part 5)

```
                   *   ***    *    **  ** *** **       ***       *** **  ***   **
HSV-1   ACGGCAATCGTGTACGTCGTCCGCACATCACAGTCGGCGGCAGCGTCATCGGCGGGTAACGC   1740
HSV-2   ACCGCGGTAGTGTACCTCACCCACGCCTCCTCGGTGCGCTATCGTCGGCTGCGGTAACTC
                                                      HSV-1 gC; HSV-2 gF
                                                      termination codons

*** *** ****  ********  ************  **  ** ***** *** ****** *
HSV-1   GAGACCCCCCCCGTTACCTTTTTAATATCTATATAGTTTGGTCCCCCTT---CTATCCCG        1800
HSV-2   CGGGGCCGGGCCCGGCCCGGCCGGT-TGTCTTCTTT-TCCACCCCTTCCGTCCCCGTACCC.
        *                         *  **    ****** *     *         *
HSV-1   CC--------------CACGCTGGGCGCTATAAAGCC-GCCACCCTCTC                   1860
HSV-2   ACCACACCCCACCCCCGCCCCCCGCGGGCGTTATAAGC-CGCCGCACTCGC
                                 "TATA 2"

**  ******* *  ******    *     *        ***   ** ***  *** **
HSV-1   TTCCCTCAGGTC---ATCCTTGGTC-GATCCCGAACGAGACACGGCGTGGAG---CAAAA        1920
HSV-2   TTTTCCACCGGAAAATCCTCGGCCCGATCC-GAACGGCGCACGCCGGTGGGCGTGGGCTCCAAA

****  **** *   **** * ** * ** ***  *   ****  ** ****** *****
HSV-1   CGCCTCCCCCTGAGCC-GCTTTCCTACCAACACACCGGCATGCC---T-CT--G-----         1980
HSV-2   CGCCTCCGGAAGAGAGCGCCCCCGCCCCGGAT-ATTCAAGCCCGGTGGTGCTATGGCTTT
                                             HSV-2 second open reading
                                                   frame initiation codon

*    *  **    *  *   ** **           *** ** *  * *****
HSV-1   -CGGGCATCGGAACAGCC-TACCGGCCCCTGGGCCCCGGGACACCCCCATGCGCGGGCTCG       2040
HSV-2   CCGTGCTTCGGGACCGCCTACCAGCCCGCCTACCAGCCCGCCCCCGCCCCCGGCGGGCTCG
                                                730 bp HSV-1 mRNA
                                                     initiation codon
```

Fig. 13 (Part 6)

```
              *** *   *    *    *  *   *    *    *    ***  *  *  *
HSV-1   GCTCCCCGCCGCGGCCTGGGTTGGGCTGCGTCGGGACCATCATCGGGGGAGTTGTGATCATTGC    2100
HSV-2   TGTTCCGGCCGTGGCCTGGATCGGGCGTCGGAGCGGATCGTCGGGGCCTTTGCGCTCGTCGC
            *   *    *   *    *  * * *    *     *      *          *
HSV-1   CGCGTTGGTCCTCGTGCCCTCGCGGGGCCTCGTGGGCACTTTCCCCATGCGACAGCGGATG     2160
HSV-2   CGCGTTGGTTCTCGTACCCCTCGGTTCCTCGTGGGGACTCTGCCGTGCGACAGCGGCTG
            *      *** *    *  *    *  *    * *    *             *
HSV-1   GCACGAGTTCAACCTCGGGTGCATATCCTGGGATCCGACCCCCATGGAGCACGAGCAGGC     2220
HSV-2   GCAGGAATTCAACGCGGGATGCGTCGCGTGGGACCCCACCCCGTCGAGCACGAGCAGGC
                           *   *        *       *   *     *   *   *
HSV-1   GGTCGGGCGGGCTGTAGCGCCCCCGGGACCCTGATCCCCCGGCGCGGCTGCCAAACAGCTGGC     2280
HSV-2   GGTCGGGCGGGCTGCACGCGCCCGGCGCGGCCACCCTTATCCCCGTGCGGCCGCCAAGCACCTGGC
            ** **    *       *   *      *  *      *   *      *    *
HSV-1   CGCCGTCGCACGCGTCCAGTCGGCAAGATCCTCGGGCTACTGGTGGGTGAGCGGAGACGG     2340
HSV-2   CGCTCTGACACACGGCGTCCAGGCGGAGAGATCGTCGGGTTACTGGTCGGGTGAACGGAGACGG
            *      *    *  *    *     * **     * *     *    *
HSV-1   CATTCGGGGCCCGCCTCGCGGCTCGTCGGGCTTGGCGGTTATTGACCAGTTTTGCGAGGA     2400
HSV-2   CATCCGGACCTGTCTGAGACTCGTCGACAGCGGTCAGTGGCATCGACGAGTTTTGCGAGGA
                                              *
HSV-1   GCCCGCCCTTGCGCATATGCTACTATCCCCGCAGTCCCGGGGGCTTTGTTCAGTTTGTAAC     2460
HSV-2   GCTC
             *
HSV-1   TTCGACCCGCAACGCGCTGGGGGCTGCCGTGA                                  2491
```

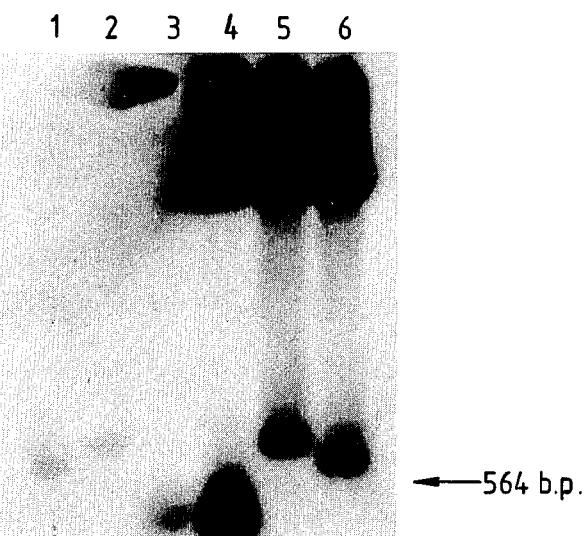

Fig.15(Part 1)

```
              C       C    C CC  CCCN    CN  C CC CCCN    CN  C CNC    C CC
              *       *    * **  ****    **  * ** ****    **  * ***    * **
HSV-1 gC    1 MAPGRVGLAVVLWGLLWLGAGVAGGSETASTGPTITAGAVTNASEAPTS
HSV-2 gF      MALGRVGLAVGLWGLLWVGVVVLANGAPGRTIITVGPRGNAANAAPS

************************       NCNCC  N    N CNCN  CCNC
                ************************       *****       * **** ****
HSV-1 gC   50 GSPGSAASPEVTPTSTPNPNNVTQNKTPTEPASPPTTPKPTSTPKSPPT
HSV-2 gF   48 ------------------------VPRNASAPRTTPTPPQPRKATKS

NCCNC   NNN      C   C CCC    N N C
              *****   ***      *   * ***    * * *
HSV-1 gC  101 STPDPKPKNNTTPAKSGRPTKPPG-PVWQDRRDPLARYGSRVQIRQRFR
HSV-2 gF   71 KASTAKPAPP--P-KTG-PPKTSSEPVRQNRHDPLARYGSRVQIRQRFPN

C C          CCCCNCC CC    N  C    CN     C CC       N
                * *          ******* **    *  *    **     * **       *
HSV-1 gC  150 STRMEFRLQIWRYSMGPSPPIAPAPDLEEVLTNKIAPPGGLLVYDSAPN
HSV-2 gF  117 SQRTESRLQIWRYATATDAEIGTAPSLEEVMNRYSAPPGGQLVYDSAPNR

C                  C  CN   C   CN       C CCC       NC
              *                  *  **   *   **       * ***       **
HSV-1 gC  200 TDPHVLWAEGAGPGADPPLYSVTGPLPTQRLIIGEVTPATQGMYYLAWGR
HSV-2 gF  167 TDPHVIWAEGAGPGASPRLYSVVGPLGRQRLIIEELTLETQGMYYWVWGR
```

Fig. 15 (Part 2)

```
             C  N NC                   C      CC  C              C    N NC
             *  * **                   *      **  *              *    * **
HSV-1 gC 250 MDSPHEYGTWVRVRMFRPPSLTLQPHAVMEGQPFKATCTAAAYYPRNPVE
HSV-2 gF 217 TDRPSAYGTWVRVRVFRPPSLTIHPHAVLEGQPFKATCTAATYYPGNRAE

N    C   N     CC    C                            C
                 *    *   *     **    *                            *
HSV-1 gC 300 FDWFEDDRQVFNPGQIDTQTHEHPDGFTTVSTVTSEAVGGQVPPRTFTCQ
HSV-2 gF 267 FVWFEDGRRVFDPAQIHTQTQENPDGFSTVSTVTSAAVGGQPPRTFTCQ

C               CCC  C                       C     CCN C
               *               ***  *                       *     *** *
HSV-1 gC 350 MTWHRDSVTFSRRNASGLALVLPRPTITMEFGVRHVVCTAGCVPEGVTFA
HSV-2 gF 317 LTWHRDSVSFSRRNASGTASVLPRPTITMEFTGDHAVCTAGCVPEGVTFA

C       C              CC   NC  C         C      C   N C
                 *       *              **   **  *         *      *   * *
HSV-1 gC 400 WFLGDDPSPAAKSAVTAQESCDHPGLATVRSTLPISYDYSEYICWLTGYP
HSV-2 gF 367 WFLGDDSSPAEKVAVASQTSCGRPGTATIRSTLPVSYEQTEYICRLAGYP

N                                N CCC    CC CC    CC   C
                   *                                * ***    ** **    **   *
HSV-1 gC 450 AGIPVLEHHGSHQPPPRDPTERQVIEAIEWVGIGIVLAAGVLVVTAIVY
HSV-2 gF 417 DGIPVLEHHGSHQPPPRDPTERQVIRAVEGAGIGVAVLVAVVLAGTAVVY

CCCC  NN N NN
             ****  ** * **
HSV-1 gC 500 VVRTSQSRQRHRR
HSV-2 gF 467 LTHASSVRYRRLR
```

Fig. 15 (Part 3)

```
                      **********  C   C   C       C  C  C CCCCC
                      **********  *   *   *       *  *  * *****
HSV-2 730bp ORF    1  MAFRASGPAYQPLAPRPPPARARVPAVAWIGVGAIVGAFALVAALVLVP
HSV-1 730bp ORF    1  ----------MRARLPAAAWGVGTIIGGVVIIAALVLVP

C  C  C       C   C  CC          C                C   C  CC      CCCCC
                   *  *  *       *   *  **          *                *   *  **      *****
HSV-2 730bp ORF   50 PRSSWGLCPCDSGWQEFNAGCVAWDPTPVEHEQAVGGCSAPATLIPRAAA
HSV-1 730bp ORF   31 SRASWALSPCDSGWHEFNLGCISWDPTPMEHEQAVGGCSAPATLIPRAAA

C  CC  CC      N          CN          C    C
                    *  **  **      *          **          *    *
HSV-2 730bp ORF  100 KHLAALTRVQAERSSGYWWVNGDGIRTCLRLVDSVSGIDGFCEEL
HSV-1 730bp ORF   81 KQLAAVARVQSARSSGYWWVSGDGIRARLRLVDGVGGIDQFCEEPALRIC

HSV-1 730bp ORF  131 YYPRSPGGFVQFVTSTRNALGLP
```

MOLECULARLY CLONED DIAGNOSTIC PRODUCT AND METHOD OF USE

This application is a continuation of application Ser. No. 587,763, filed Mar. 9, 1984, now abandoned.

This is a continuation-in-part of application Ser. No. 527,916, filed Aug. 30, 1983, now abandoned, and of application Ser. No. 547,552 filed Oct. 31, 1983, now abandoned.

This invention relates to immunological diagnostic products derived from recombinant DNA technology, and to their methods of use.

Analysis of the immune response to a variety of infectious agents has been limited by the fact that it has often proved difficult to culture pathogens in quantities sufficient to permit the isolation of important cell surface antigens.

The detection of HSV-1 IgG and IgM antibodies has been performed by enzyme-linked immunosorbant assay (ELISA) (A,B). In both of these techniques, extracts of HSV-infected cells are disclosed for use as antigens. The disadvantages of using live antigen in a laboratory environment are well known, including the requirement of culturing and containment of the infectious agents.

The advent of molecular cloning has overcome some of these limitations by providing a means whereby gene products from pathogenic agents can be expressed in virtually unlimited quantities in a non-pathogenic form. Surface antigens from such viruses as influenza (1), foot and mouth disease (2) hepatitis (3), vesicular stomatitis virus (4), rabies (5), and herpes simplex viruses (6) have now been expressed in E. coli and S. cerevisiae, and, in the future, promise to provide improved subunit vaccines. The expression of surface antigens in lower organisms is not entirely satisfactory in that potentially significant antigenic determinants may be lost by virtue of incomplete processing (e.g., proteolysis, glycosylation) or by denaturation during the purification of the cloned gene product.

This is particularly true in the case of membrane proteins, which, because of hydrophobic transmembrane domains, tend to aggregate and become insoluble when expressed in E. coli. Cloned genes coding for membrane proteins are known in mammalian cells where the host cell provides the factors necessary for proper processing, polypeptide folding, and incorporation into the cell membrane (7,8). While these studies show that membrane proteins can be expresses on the surface of a recombinant host cell, and for example (8), that a truncated membrane protein lacking the hydrophobic carboxy-terminal domain can be slowly secreted from the host cell rather than be bound to it, they describe the transitory expression of the cloned gene for membrane-bound proteins and the detection of such protein by staining with its complementary labelled antibody. There is no suggestion in these publications that the membrane-bound protein could be used as an immunological diagnostic reagent. Furthermore, even if there were such a suggestion, the instability of the cell lines renders the described membrane-bound proteins to be a scientific curiosity, not a useful, practical diagnostic product.

Herpes Simplex Virus (HSV) is a large DNA virus which occurs in two related, but distinguishable, forms in human infections. At least four of the large number of virus-encoded proteins have been found to be glycosylated and on the surface of both the virion and the infected cells (9). These glycoproteins, termed gA/B, gC, gD, and gE, are found on both HSV type 1 (HSV-1) and HSV type 2 (HSV-2), while in the case of HSV-2, an additional glycoprotein (gF) has been reported to be found (10). Although their functions are not fully understood, these glycoproteins appear to be involved in virus attachment to cells, cell fusion, and a variety of host immunological responses to virus infection (11). Although HSV-1and HSV-2 show only about 50 percent DNA sequence homology (12), the glycoproteins appear to be, for the most part, type-common. Thus, gA/B, gD, and gE show a large number of type common antigenic determinants (13–16), while gC, which was previously thought to be completely type-specific (17,18), has also been found to possess some type-common determinants. Type specific antigenic determinants can, however, be demonstrated using monoclonal antibodies for some of the glycoproteins (10,19), showing that some amino acid changes have occurred since HSV-1 and HSV-2 diverged.

One of the most important glycoproteins with respect to virus neutralization is gD (11). Considerable evidence has been adduced strongly suggesting that the respective gD proteins of HSV-1 and HSV-2 are related. For example, recombination mapping has localized the respective genes to colinear regions in both virus genomes. Amino acid analysis showed gross homology between the two proteins. The gD proteins induce neutralizing antibodies to both type 1 and type 2 viruses in a type-common manner (19-21). In addition, most monoclonal antibodies generated to these glycoproteins are type common, also suggesting a high degree of structural relatedness between the two types of glycoproteins (20). Some monoclonal antibodies, however, were found to react type-specifically, suggesting significant differences between the proteins (19). Peptide maps of the proteins also unambiguously revealed such differences (22). These results although suggesting that these polypeptides are related, are insufficient to indicate exactly how close the relationship is.

In order to examine the nature of the type-commonality of HSV-1 and HSV-2 gD proteins, the DNA sequences of the gD genes from HSV1 and HSV-2 were determined. The derived amino acid sequences showed similarity. The resultant derived protein sequences were also analyzed for structural differences by using a program designed to determine hydrophobic and hydrophilic regions of the protein. This analysis demonstrated a high degree of conservation on a gross structural level. Although several amino acid substitutions were found between the two glycoproteins, the vast majority of these substitutions were conservative, suggesting an important structural requirement of this glycoprotein to the virus.

In the light of this information about the structure of the gD protein, as described more fully herein, it was decided to express the gD protein DNA in mammalian cells to see whether such was possible, and if possible, whether the expressed protein would bind to the host cell membrane, and whether a truncated form of protein lacking the membrane-binding domain would be secreted from the host cell, and in either of the latter cases whether the expression product proteins could bind with antibodies effective against HSV-1 and/or HSV-2. This procedure is fully described in copending application Ser. No. 527,917, filed Aug. 30, 1983, incorporated herein by reference. As shown in that application, such expression product proteins are capable of raising antibodies effective against HSV1 and/or HSV-2 and are thus useful as a vaccine. As the results herein will show, such expressed proteins obtained by recombinant DNA processes, being capable of recognition by antibodies against HSV-1 and/or HSV-2, also are useful diagnostic products for detecting and/or measuring the presence of antibodies characteristic of those viruses. Mapping studies (22a) suggest that the protein sequence derived from the HSV-2 genome corresponds to gF, the HSV-2 homologue of HSV-1 gC.

HSV-1 gC has been considered to be type-specific without homology in HSV-2 since antibodies against this glycoprotein were found to react almost exclusively with HSV-1 gC (17). In addition, no detectable immunological reactions could be demonstrated between HSV-1 gC and antisera made against HSV-2 virus (18). A protein having the same electrophoretic mobility as HSV-1 gC has been demonstrated in HSV-2, however it did not map colinearly with HSV-1 gC (35).

In contrast to HSV-1, HSV-2 appears to encode yet another glycoprotein, termed gF (22b,10,22c,22d). Although the HSV-2 gF had an electrophoretic mobility which was much faster than HSV-1 gC, mapping studies with recombinant viruses revealed that this protein was encoded by a region of the HSV-2 genome which was approximately colinear with the gene for HSV-1 gC (22c,22d). In addition, it has been recently demonstrated that a monoclonal antibody against HSV-2 gF will cross-react weakly with HSV-1 gC (22f) and that a polyclonal antiserum made against HSV-1 virion envelope proteins precipitated gF (22d), suggesting a possible structural homology between the two glycoproteins. Thus, it appeared that a possible homologue to HSV-1 gC was the HSV-2 gF protein. This relationship was investigated in accordance with the present invention.

BRIEF DESCRIPTION OF THE DRAWINGS

FIGS. 1A and 1B show the DNA and deduced amino acid sequences of the HSV-1 and HSV-2 gD genes and surrounding flanking regions;

FIG. 3 is a diagram of the plasmid pgD-dhfr, constructed for the expression of a membrane-bound form of HSV-1 glycoprotein D;

FIG. 8 is a diagram of the expression plasmid pgDtrunc-dhfr for a secreted form of HSV-1 gD protein.

FIG. 13 shows the DNA sequence derived from pgC$_2$SA12.9 compared with the DNA sequence of the HSV-1 gC region.

FIG. 14 illustrates southern blot analysis of HSV-2 genomic DNA and pgC$_2$Sa 12.9 DNA.

FIG. 15 illustrates translation of the HSV-2 large open reading frame and comparison with the HSV-1 gC amino acid sequence.

SUMMARY OF THE INVENTION

Figure 2:
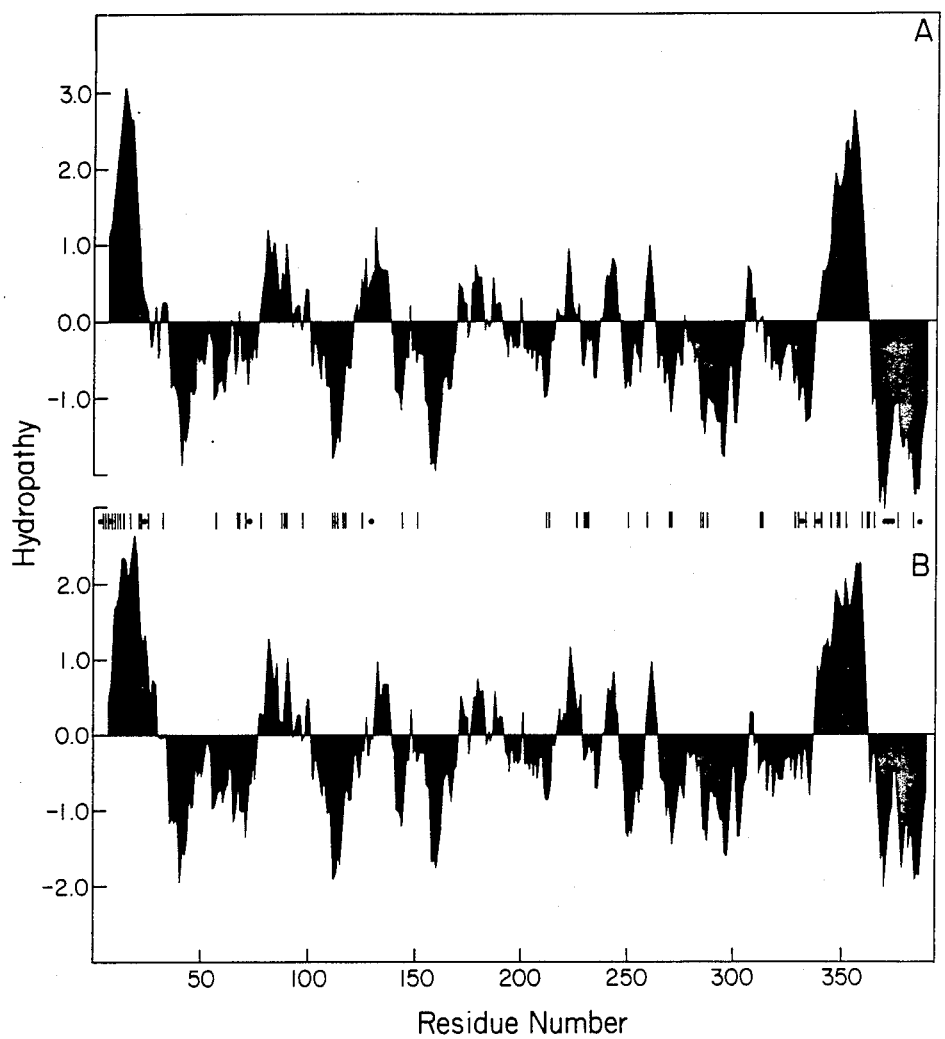
FIG. 2 shows a hydropathy analysis of the gD proteins from HSV-1 and HSV-2 proteins.

In accordance with the present invention, recombinant DNA technology is utilized to provide gene products in large quantities in a non-pathogenic form for use as diagnostic agents. The advantages of such gene products are illustrated by reference to the diagnosis of certain infections such as HSV. Present methods used to diagnose HSV include (a) the culture of clinical isolates, (b) the use of reagents prepared from live viruses, or (c) the use of monoclonal antibodies coupled to a label such as fluorescence or enzyme. The first method is labor-intensive and typically requires several days to obtain a result. The second approach often is not practical because it requires biochemical procedures beyond the range of most clinical laboratories. The third method depends upon the detection of an open lesion and the availability of detection means, for example, a fluorescent microscope or a fluorescent label. Because of this, laboratory confirmation of clinical diagnosis commonly is not employed.

The present system employs a diagnostic product (as defined below) comprising a polypeptide with antigenic determinants capable of specifically binding complementary antibody. In one embodiment, the polypeptide is functionally associated with the surface membrane of a recombinant host cell capable of its production. In a typical instance, such functional association comprises a binding of the polypeptide with the surface membrane so that the polypeptide projects through the membrane. The recombinant cell line is derived from a stable, continuous line for the diagnostic product to be supplied on a commercial scale.

In another embodiment, the diagnostic product comprises a polypeptide with the same antigenic determinants, but which is not functionally associated with the surface membrane. As set out in more detail below, one such polypeptide is a truncated, membrane-free derivative of a membrane-bound polypeptide. The derivative is formed by omission of a membrane-binding domain from the polypeptide, allowing it to be secreted from the recombinant host cell system in which it has been produced.

In another embodiment, the polypeptide is formed first in functional association with a surface membrane and thereafter the polypeptide is dissolved, preferably in a non-ionic surfactant, to free the polypeptide of the membrane.

As more fully set out below, the diagnostic product of the present invention is utilized in place of the counterpart derived from a live pathogen in analogous immunoassays. In that regard, a commercial diagnostic test kit would include the above diagnostic products with a variety of other immunological products, at least one of which is labeled, for the detection of its complementary antibody or other antigen. The system has been described with respect to the molecular cloning of the gD proteins from HSV-1 and HSV-2, which possesses sufficient antigenic determinants to render it capable of specifically binding complementary antibody, namely antibody to HSV-1 and HSV-2. The specific techniques for cloning, sequencing and expression of the HSV-1 gD protein are set forth in Example 1 below. As set forth therein, the hydropathy plot of FIG. 2 revealed a hydrophilic carboxy-terminal domain preceded by a hydrophobic region. This structure is characteristic of a membrane-bound glycoprotein. Its function is to anchor the protein in the cellular and viral membranes.

To examine the relatedness between HSV-1 and HSV-2, it has been determined that a DNA sequence of a 2.29 kb region of the HSV-2 genome is colinear with the HSV-1 gC gene. Translation of a large open reading frame in this region demonstrates that a protein which has significant homology to HSV-1 gC is encoded in this region. It is suggested that this region encodes the HSV-2 gF gene and that the gF protein is the HSV-2 homologue of HSV-1 glycoprotein C.

As set forth herein, a glycoprotein in HSV-2, formerly referred to as gF, is more properly designated a gC. (The terms "HSV-2 gF", "HSV-2 gC" and "gC-2" will be used interchangeably for this product.) It has been found that a segment of gC-2 is type common to HSV-1 gC (or gC-1) while another segment is type specific.

A diagnostic product formed of a fragment of gC-2 containing the type-specific segment but excluding the type-common segment permits the detection of HSV-2 in contradistinction to HSV-1. If the diagnostic test is positive, the subject has HSV-2. Using this test in combination with another test which is common for HSV-1 and HSV-2 would permit diagnosis of HSV-1. For example, a positive reading using gD in a diagnostic test corresponds to the presence of HSV-1 and/or HSV-2 virus. If type-specific gC-2 test is also positive, the subject has HSV-1 and HSV-2; if negative, the subject only has HSV-2. Thus, for the first time, a diagnostic test has been devised which is capable of distinguishing HSV-1 from HSV-2.

Other known glycoproteins of HSV-1 or HSV-2, e.g. gA, gB or gE, or others not yet identified, may be used for diagnostic products for HSV-1 or HSV-2. If such glycoproteins include type specific determinants for HSV-1 or HSV-2, then analogous recombinant techniques to those set forth herein with respect to gC and gD may be used to form such glycoproteins into diagnostic products capable of distinguishing HSV-1 from HSV-2. If the glycoproteins also include type-common determinants, then the same recombinant techniques set forth herein with respect to gC-2 production may be used to isolate the type-specific fraction isolated from the type-common fraction for specific diagnosis of HSV-1 or HSV-2. If the glycoprotein only includes type-common fractions, then it may be produced by recombinant techniques in a manner analogous to gC.

It is believed that only certain techniques of molecular cloning produce a polypeptide with suitable specific antigenic determinants for detection by its complementary antibody. Thus during formation, the polypeptide must be formed in a manner to fold properly, to be glycosylated and to be correctly processed. As illustrated in Example 1, one technique for accomplishing the production of a cell with these desired characteristics is for the polypeptide to be molecularly cloned in a manner to be functionally associated with the surface membrane of a recombinant host cell. For this purpose, it is believed necessary to use a eukaryotic host cell system, and preferably a mammalian cell system. Thus, for example, the HSV-1 glycoprotein D expressed in Chinese Hampster Ovary cells, (CHO) produces a membrane-bound gD protein with suitable antigen characteristics. Other suitable recombinant host cell systems include mouse L cells, etc.

As used herein, the term "recombinant" refers to cells which have been transfected with vectors constructed using recombinant DNA technology and thus transformed with the capability of producing the polypeptide hereof. "Functional association" is meant being bound to the membrane, typically by projecting to both sides of the membrane, in such manner as to expose antigenic determinants folded in a native conformation recognizable by antibody elicited against the native pathogen. "Membrane-bound" in reference to polypeptides hereof refers to a class of polypeptides ordinarily produced in eukaryotic cells and characterized by having a signal sequence which is believed to assist its secretion through various cell membranes as well as a membrane-binding domain (usually hydrophobic in nature and occurring at the C-terminal end) which is thought to preclude its complete secretion through the cell membrane. As such, it remains functionally associated or bound to the membrane. This invention is particularly directed to the exploitation of those membrane-bound polypeptides associated with pathogenic organisms, e.g., herpes virus.

Once the antigenic determinants of the polypeptides of the present invention are provided by functional association with the surface membrane, thereafter, the membrane may be removed from the polypeptides without destroying the antigenic characteristics. Thus, for example, the membrane-bound polypeptide may be removed from the membrane by solubilization with a suitable solution, preferably one containing a non-ionic surfactant, to remove the polypeptide from the membrane. An advantage of doing this is to isolate the polypeptide from extraneous cellular material, raising potential potency in its use in a vaccine. A technique for removing the membrane from the polypeptide is described below.

In another embodiment, membrane-free preparations may be obtained by creation of a secretion system. As described in more detail below, such secreted polypeptide possesses at least some of the antigenic sites necessary for antibody stimulation.

In another embodiment, the membrane may be removed by secreting the polypeptides from its membrane-bound environment. It has been found that such secreted polypeptide possesses at least some of the antigenic sites necessary for antigenic detection. A suitable technique for accomplishing this is described in Example 3 below.

There are a number of known techniques for the determination of an unknown quantity of antigen or antibody in the biological fluid, such as serum, urine, or from skin samples or the like. In principle, the present invention utilizes such known techniques but substitutes certain molecularly cloned diagnostic reagents of a type set forth above in the otherwise known procedures. Accordingly, the procedures themselves will be described only generally with reference being made to conventional immunology text for the details of the procedures. It would be well known to skilled workers in the field how to utilize the novel diagnostic products of the present invention in conventional immunological techniques.

For simplicity of description, the general term "diagnostic product" will be used in describing the antigen-functional product of the present invention. The term "diagnostic product" is defined as a polypeptide with antigenic determinants capable of specifically binding corresponding antibody induced by the pathogen organism and being formed in a recombinant host cell capable of its production and derived from a stable, continuous recombinant cell line. The polypeptide either may be functionally associated with a surface membrane of the recombinant host cell or not.

In the latter instance, the polypeptide is typically in truncated form and formed by a secretion from the recombinant host cell system, or is freed of the membrane by dissolution of the membrane in a solution such as or solution of a non-ionic surfactant.

In general, the diagnostic products may be used for the detection of either antibody or antigen in a biologically derived fluid sample. For the detection of antibody, the fluid sample is contacted with the diagnostic product to bind the diagnostic product with complementary antibody in the fluid sample, and such binding is detected and, preferably, also measured. For the detection of antigen, the fluid sample is contacted with the diagnostic product having the same antigenic determinants as the sample antigen. Then, the sample antigen is detected, and, preferably measured, using a competitive assay.

As set forth above, one known scheme utilizes extracts of HSV-infected cells as antigen in an ELISA sandwich-type technique. The general procedure of such techniques may be used in the present invention.

Referring to the system of detecting antibody, the diagnostic reagent is typically formed by being bound (e.g. by adsorption or covalent bonding) to a solid surface, typically the surface of a well or test tube.

Other suitable solid surfaces can include a surface capable of immobilizing the diagnostic reagent such as a bead.

The solid surface to be layered with the diagnostic product should be sufficiently impermeable to liquid to permit effective removal by washing of unbound reagent. It should also permit binding of the diagnostic reagent. If covalent bonding is desired, suitable surfaces include plastic such as polystyrene. Suitable coupling techniques between the surface and diagnostic region are set forth in Bennich et al., U.S. Pat. No. 3,720,760.

In the sandwich technique for the determination of an unknown antibody in a sample, the bound diagnostic product is reacted with the antibody and with soluble labeled anti-antibody capable of specifically binding the complementary antibody in the sample. In this manner the sample antibody is bound on the solid surface both to the diagnostic product and the labeled anti-antibody in a sandwich. Then the solid surface is washed to remove unreacted labeled anti-antibody. Thereafter, the labeled anti-antibody on the solid surface or in the wash solution is detected as an indication of the antibody quanitity in the sample. The reaction on the solid surface forms a reaction product in order, comprising solid surface*diagnostic products*sample antibody*labeled anti-antibody. The "*" signifies a bond. For example, the bond between the surface and diagnostic product may be a covalent bond or an adsorptive bond. Bonds between the diagnostic product and the sample antibody and between the sample antibody and the labeled anti-antibody comprise immunological bonds.

As is well known, in ELISA, the label is an enzyme which is colorimetrically detected after reaction with its complementary substrate to a colored form. Such colorimetric detection has the advantage of not requiring instrumentation. Other known labels include radioactive or fluormetric ones which are detected by instrumentation.

Labeling of the anti-antibody with enzyme is preferably performed by conventional techniques of linkage by one or more covalent bonds. Such covalent bonds may be accomplished by the addition of external coupling or bridging molecules, or by direct condensation of existing side chains. Functional bridging agents for accomplishing this purpose are well known in the art.

The system of the present invention is also applicable to the so-called competitive binding technique for the immunoassay of antibodies to be detected in a biologically derived fluid. In this instance, the diagnostic product is also bound in a layer to a solid surface as set forth above. This solid phase is contacted with the biologically derived fluid containing the antibody to be detected and with free soluble labeled antibody of the same immunological type as the antibody to be detected. A competitive immunological reaction is caused to occur between the bound diagnostic product and both (a) the antibody in the sample to be detected, and (b) the enzyme labeled antibody. Thus, the concentration of antibody to be detected in the biologically derived fluid is inversely proportional to the enzyme-labeled antibody bound to the solid surface.

After the above competitive reaction, the solid surface is separated from the liquid phase. When a test tube or a well is employed, this constitutes washing of the test tube or well. This washing removes unbound-labeled antibody from the surface.

Then, the labeled antibody in the solid or liquid phase is detected as a measure of the sample antibody. Suitably this is accomplished by contacting the separated solid phase with a solution containing soluble substrate for the enzyme to cause the substrate to be converted to a colored form.

The above sandwich or competitive techniques are particularly effective for measuring antibodies to pathogen in a biologically derived sample in diagnosis wherein the presence of the antibodies in the sample is an indication that the patient has been infected with the pathogen. Thus, for example, a measure of antibodies to HSV is an indication that the patient has been infected.

Other pathogenic antibodies to which the invention is applicable following a viral infection are adenovirus, coxsackie, cytomegalovirus, Epstein-Barr, feline leukemia virus, hepatitis, hog cholera, influenza, measles, New Castle disease virus, parainfluenza, rabies, respiratory syncytial virus, rotavirus, rubella, sendai, varicella. Parasitic infections include amebiasis, babesia, cysticercosis, echinococcosis, Leishmaniasis, onchocerciasis, malaria, viceral larval migrans, toxoplasmosis, trypanosomiasis, trichinosis, and schistosomiasis. Other applications of the present invention extend into the area of autoimmune diseases where the product comprises a membrane-bound protein from the host and is used to measure antibodies directed against that protein, e.g. the acetylcholine receptor protein.

The diagnostic products of the present invention are also applicable to the determination of any polypeptide or protein, pathogenic or not, in the biologically derived sample with the same antigenic determinants as the molecularly cloned diagnostic product. For example, the system is useable for the determination in a serum sample of human hormones, such as human growth hormone and insulin-like growth factors, blood protein such as human tissue plasminogen activator (tPA); interferons, and the like.

One technique which may be employed for the detection of such proteins, designated antigens, is directly analogous to the competitive technique described above. Antibodies are bound to the solid surface instead of the diagnostic product of the present invention. In the competitive technique, the diagnostic product is labeled as described above, such as with enzyme, and mixed with the solid-bound antibody and the serum sample containing the protein with antigenic determinants to be measured. A competitive immunological reaction occurs between the immobilized antibody and both the antigen to be detected and the enzyme-labeled diagnostic product. The concentration of the antigen to be detected is inversely proportional to the enzyme-labeled diagnostic product bound on a solid surface.

After the competitive reaction, the solid phase is separated from the liquid phase and the labeled diagnostic product is measured.

The linking of the label to the diagnostic product may be accomplished by the aforementioned conventional techniques. For example, an enzyme label may be linked to the gD protein by use of gluteraldehyde cross-linking agent.

In another technique for measuring antigen in a sample, a first competitive-type binding step is followed by a second sandwich-type binding step. In the first step, the diagnostic product is bound to a solid surface as set forth above. It is mixed with a liquid sample containing the unknown antigen to be determined and with a known quantity of complimentary antibody. A competitive reaction is set up between the free sample antigen and the diagnostic product on the surface. Then the solid surface is washed and labeled anti-antibody immunologically reactive with the antibody on the solid surface is added to the system. This step comprises a sandwich technique in which a reaction product is formed in order, comprising solid surface*diagnostic products*antibody*labeled anti-antibody. The amount of labeled anti-antibody bound to the antibody is a measure of the unknown antigen in the liquid sample.

Test kits utilizing the aforementioned diagnostic product are useful in the diagnosis of antigens or antibodies by the above techniques. One such kit includes the diagnostic product and labeled anti-antibody capable of specifically binding antibody complementary to the antigenic determinants of the polypeptide of the diagnostic product. This test kit is suitable for a sandwich type ELISA for sample antibody.

Another test kit may include the diagnostic product, labeled anti-antibody and unlabeled antibody complementary to the antigenic determinants of the polypeptide. This test kit is effective for the so-called competitive sandwich technique for the determination of sample antigen.

A further test kit includes the diagnostic product together with labeled antibody complementary to the antigenic determinants of the polypeptide of the diagnostic product. This test kit is suitable for the determination of antibody in the sample by a competitive technique.

The diagnostic product in the test kit may be in solution or bound to the solid surface in the form in which it is to be used. For example, the diagnostic product may be layered onto the inner surface of a test tube or well of a multi-welled sheet for direct use in the ultimate immunoassay. This form highlights the advantages of stability of the molecularly cloned diagnostic product in comparison to the use of the live virus. Of course, it greatly facilitates testing in a laboratory or in a doctor's office because the molecularly cloned product is not infectious as would be the live pathogen used in immunoassays of the prior art.

The following Examples are illustrative of the present invention.

EXAMPLE 1

This example illustrates the method of formation and characterization of the gD proteins from HSV-1 and HSV-2 proteins.

Detailed Description (Examples)

Virus Growth and Viral DNA Isolation

HSV1 (strain Hzt) and HSV2 (strain G) were grown on Hep 2 cells at 37° C. and at 33° C., respectively. The viral DNA was isolated from infected cell cultures by proteinase K digestion and CsCl banding (23).

Cloning of the gD Genes of HSV1 and HSV2

Previous mapping and cloning studies had localized the HSV1 gD gene to a ~6.6 kb BamHI fragment (6,24). HSV1 DNA was cleaved with BamH1 and the 6-7 kb region was isolated by agarose gel electrophoresis. This fragment was ligated into BamHI-digested pBR322, and the resultant mixture was used to transform E. coli strain 294 (ATCC No. 31446). The ampicillin resistant, tetracycline sensitive plasmids were screened for the proper HSV1 fragment by restriction enzyme digestion. The correct gD containing Sst1 fragment was subcloned into Sst1-digested plasmid pFM3 (European Pat. Application Publication No. 0068693; Jan. 5, 1983).

Although the gD gene from HSV2 was previously mapped by recombination with HSV1, the exact location of this gene was unknown. Therefore, an ~10 kb HindIII fragment from the small unique region of the HSV2 genome (4) was ligated into the HindIII site of the bacteriophage lambda cloning vector 590 (25). In vitro packaged phage were plated at low density and screened by the Benton-Davis procedure with a $^{32}$P-labeled subclone of the gD gene from HSV1 (26). Positively hybridizing plaques were grown, the DNA isolated, and the gD gene localized by Southern blotting and hybridization with the $^{32}$P-labeled HSV1 gD gene (27). The positively hybridizing, HSV2 gD containing fragments were subcloned into the plasmid pUC9 (28).

DNA Sequence Determination and Computer Analysis

Various fragments from the HSV1 and HSV2 gD genes were subcloned into the m13 phage vector mp9 (29), and were sequenced by the dideoxynucleotide method of Sanger (30).

The nucleotide sequences were analyzed using the HOM program (31). The hydropathy of the deduced protein sequence was analyzed using a width of 12 and a jump of 1 (31a). Cloning of the gD Regions from HSV1 and HSV2

Other studies had localized the HSV1 gD gene to the 6.6 kb BamHI J fragment according to the nomenclature of Roizman (6,12,24). Isolation and sequencing of part of this fragment showed that this fragment contained the HSV1 gD gene. Since one might expect that the DNA sequences of the HSV1 gD gene would be relatively homologous to the HSV2 gD gene, this fragment was used as a probe for the isolation of the gD gene from the HSDV2 genome.

Since most of the genes from the HSV1 and HSV2 genomes appear to map colinearly (35), the region from the small unique region of the HSV2 genome which corresponded to the HSV1 gD region (the HindIII L fragment (12)), was cloned into a lambda phage vector. Screening of the resultant plaques with a $^{32}$P-labeled SHV1 gD gene subclone revealed positively hybridizing plaques, suggesting that there was indeed nucleic acid sequence homology between the two virus genomes in this region. Isolation of the phage DNA and subsequent Southern blot analysis revealed the region of this fragment which corresponded to the gD gene. This region was subcloned for DNA sequence analysis.

The Coding Regions

Figure 1A:
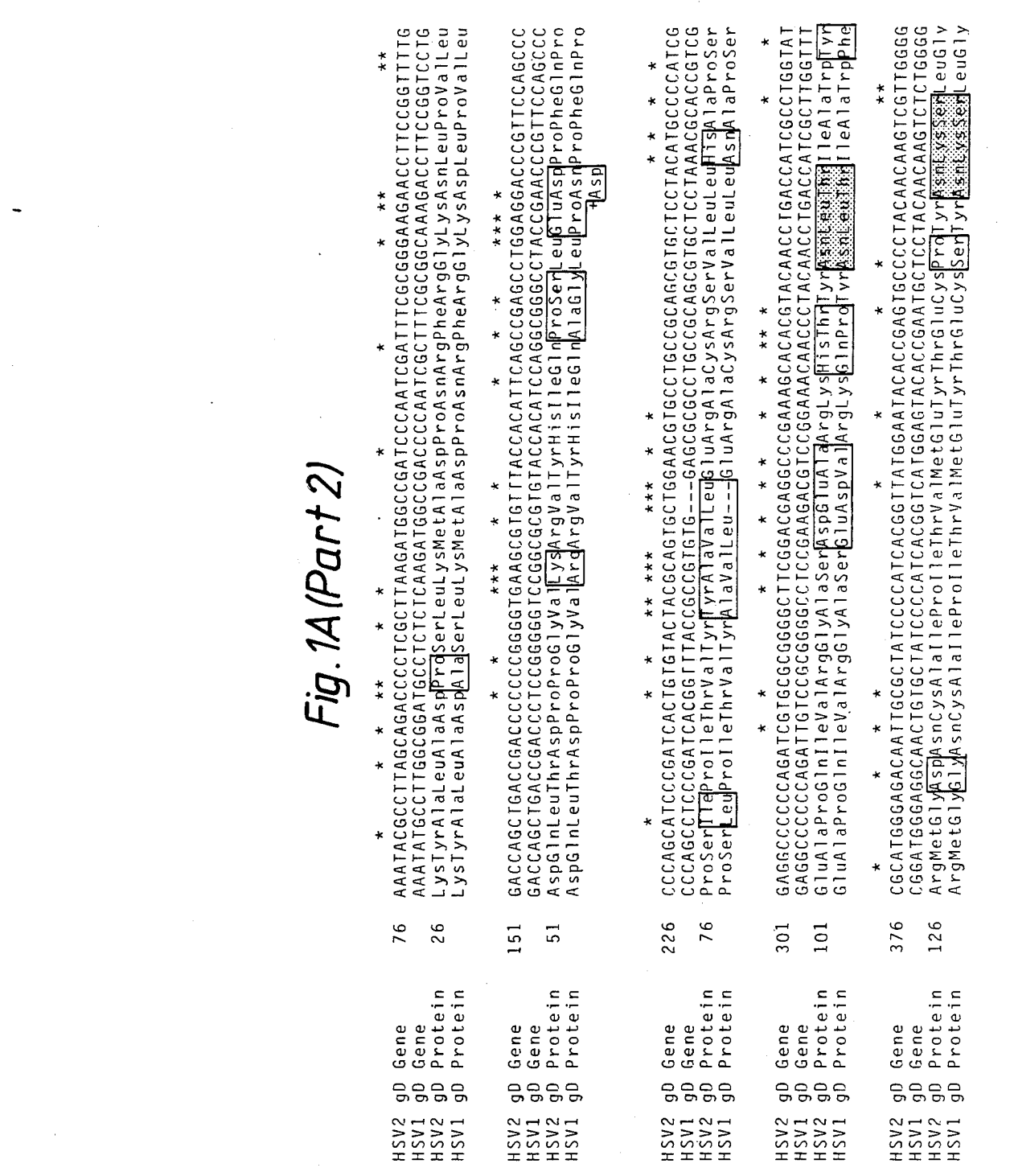

FIG. 1 illustrates the two gD DNA sequences compared with the HOM program (31). Nucleotide number 1 is chosen as the A of the ATG initiator methionine. Gaps have been introduced by the HOM computer program to maximize the sequence homologies (31). Nucleotide differences are shown by the symbol (*), while amino acid differences are shown boxed. Amino acid differences between the HSV1 gD sequence reported here, determined for the Hzt strain of HSV1, and that reported by Watson et al. (6) for the Patton strain, are depicted by the symbol (+). The start of HSV1 gD gene transcription, shown by an arrow, is from Watson et al. (32). Possible N-linked glycosylation sites are shown shaded. Two possible "TATA" sequences are shown 5' to the start of gD transcription, while a third possible "TATA" sequence is shown 5' to a second open reading frame at the 3' end of the HSV2 sequence. Two regions of non-coding sequence homology should be noted 5' to the gD genes and 5' to the second open reading frame from the HSV2 sequence.

The Hydropathy of gD Proteins

The hydropathy of each glycoprotein was analyzed using the program developed by Hopp et al. (31a). As shown in FIG. 2, a hydrophobic transmembrane domain exists at the 3+-end of the gene. Twelve amino acid long stretches were analyzed, and the average hydropathy was calculated. Residue differences between the two glycoproteins are shown, with conservative changes marked (*) and non-conservative changes marked (+). (A) HSV1 gD protein hydropathy, (B) HSV2 gD protein hydropathy.

The DNA sequence analysis demonstrates that the HSV1 and HSV2 gD proteins are 80 percent homologous. The majority of the differences found between these two proteins were in the amino and carboxy terminal regions. The amino-terminal region of these proteins contains a highly hydrophobic region which contains an arginine residue near the amino-terminal methionine. This hydrophobic domain is the signal sequence which is characteristic of secreted and membrane-bound proteins and which presumably functions to direct at least a portion of the protein into the lumen of the endoplasmic reticulum (33). A comparison of the first twenty amino-terminal amino acids showed that there were a total of 12 differences between the type 1 and type 2 genes. Virtually all of the differences, however, are conservative since they encode other hydrophobic amino acids. The exceptions are the gly-arg replacement at residue 3 and the arg-gly replacement at residue 7. Although these replacements are not conservative, they do not change the net structure of the signal domain. Both genes maintain a positively charged residue within the first 10 amino acids.

The hydropathy plot in FIG. 2 revealed a hydrophilic carboxy-terminal domain preceded by a hydrophobic region. This structure is characteristic of membrane-bound glycoproteins and has been previously found in other viral surface antigens (5,34). Its function is to anchor the protein in the cellular and viral membranes and, as such, performs an important role for virus infection. Twelve amino acid changes in this region of the gD proteins from residues 333 to 362 were found, most of which are conservative. This suggests that the only criterion for the amino acids in this region is that they be predominantly apolar in order to span the lipid bilayer. In addition, the region after the membrane domain (residues 363–375), which probably serves to anchor the protein in the membrane (33), shows 5 changes in its first 13 residues followed by a long homologous stretch. This result suggests that the initial 10–15 residues in the carboxy-terminal hydrophilic domain may only serve an anchoring function and therefore only need to be charged, while the subsequent 23 residues may serve some other function important to the gD protein specifically.

Although many other amino acid changes are found throughout these two proteins, the vast majority of the changes are conservative. This fact is underlined by the structure revealed by the hydropathy program shown in FIG. 2. As can be seen in this comparison, the two glycoproteins show very similar plots. The amino acid changes which are not conservative do not appear to change the hydropathy of the protein.

Expression of the HSV1 gD

In order to establish a permanent membrane-bound gD producing cell line, the gD containing fragment was ligated (FIG. 3) into a mammalian expression vector (36) containing the selectable marker, dihydrofolate reductase (dhfr). FIG. 3 shows a diagram of the plasmid, pgD-dhfr, constructed for the expression of HSV1 glycoprotein D. The expression plasmid consisted of the origin of replication and the β-lactamase gene (amp$^r$) derived from the E. coli plasmid pBR322 (37), a cDNA insert encoding mouse dhfr (36,38) under control of the SV-40 early promoter and a 4.6 kb HindIII to BamHI fragment containing the gD gene also under control of the SV-40 early promoter. The HindIII end of this fragment lies 74 bp to the 5' side of the initiator methionine codon and includes the mRNA cap site. The HindIII site lies 250 bp to the 3' side of the Goldberg-Hogness box of the SV-40 promoter. The coding region of the gD-containing fragment is 1179 bp long and adjoins a large (1.9 kb) 3' region which contains at least part of the glycoprotein E gene (24, 32), a translational stop codon, and a polyadenylation site.

The plasmid pgD.dhfr was constructed as follows: The 4.6 kilobase HindIII-Bam H1 fragment containing the entire gD coding sequence was isolated from the Bam H1 fragment cloned from the HSV 1 genome (see above). The 2.8 kilobase HindIII-Sal 1 fragment containing an SV40 origin-early promoter and the pBR322 ampicillin resistance gene and origin of DNA replication were isolated from the plasmid pEHBal 14. The 2.1 kilobase Sal 1-Bam H1 fragment containing a murine dihydrofolate reductase cDNA clone under the control of a second SV40 origin-early promoter was isolated from the plasmid pE348HBV E400D22 (36). These three fragments were ligated together in a triple ligation using T4 DNA ligase, and the resultant mixture was used to transform E. coli strain 294. The resultant colonies were grown and the plasmid DNA screened by digestion with Sac 2. The correct DNA construction pgd.dhfr (FIG. 3) was used for further transfection studies.

The plasmid was introduced into Chinese Hamster Ovary cells (CHO) deficient in the production of dhfr (39) using a calcium phosphate precipitation method (40). Colonies capable of growth in media lacking hypoxanthine, glycine, and thymidine were obtained and nine dhfr+ clones were analyzed. Of these, gD could be detected in five colonies using anti-HSV-1 antibodies in radioimmunoprecipitation and indirect immunofluorescence assays. One of the five lines (gD12) was designated for further study. In order to characterize the cloned gD gene product, gD12 cells were metabolically labeled with $^{35}$S-methionine or $^{3}$H-glucosamine and analyzed by radioimmunoprecipitation. The procedure used was as follows: Cells were grown in Ham's F12 medium (Gibco) supplemented with 7 percent commercially dialyzed fetal bovine serum (Gibco) penicillin (100 u/ml), and streptomycin (100 u/ml). When the cultures were approximately 80 percent confluent, the medium was removed, the cells were washed twice with phosphate buffered saline (PBS), and labeling medium (Dulbecco's modified Eagle's medium containing either one-tenth the normal concentration of methionine or glucose) was added to a final concentration of 0.064 ml/cm$^2$. Either $^{35}$S-methionine (SJ.204, Amersham Int.) (50-75 μCi/ml) or $^{3}$H-glucosamine (100 μCi/Ml) was added and the cells were grown for an additional 18-20 hr. After labeling, the medium was harvested and the cells were washed twice in PBS, and removed from the culture dish by treatment with PBS containing 0.02 percent EDTA. The cells were then solubilized in lysis buffer consisting of: PBS, 3 percent NP-40, 0.1 percent bovine serum albumin, $5 \times 10^{-5}$ M phenylmethylsulfonyl fluoride, and 0.017 TIU/ml of apoprotinin and the resultant lysate was clarified by centrifugation at 12,000×g. For immunoprecipitation reactions cell lysates were diluted 3-fold with PBS and aliqouts (typically 180 μl) were mixed with 2-5 μl of antisera and incubated at 4° C. for 30 min. Immune complexes were then adsorbed to fixed S. aureus cells by the method of Kessler (40a) and were precipitated by centrifugation at 12,000×g for 30 s. The S. aureus cells were then washed 3 times with wash buffer (PBS, 1 percent NP-40, 0.3 percent sodium dodecyl sulfate), and the immune complexes were eluted with 20 μl of polyacrylamide gel sample buffer (62.5 mM Tris-HCl buffer, pH 6.8 containing 10 percent glycerol, 5 percent 2-mercaptoethanol, 0.01 percent bromophenol blue) at 90° C. for 3 min. After centrifugation for 30 s the supernatants were applied to 10 percent polyacrylamide slab gels according to the method of Laemmli (45).

Figure 5A:
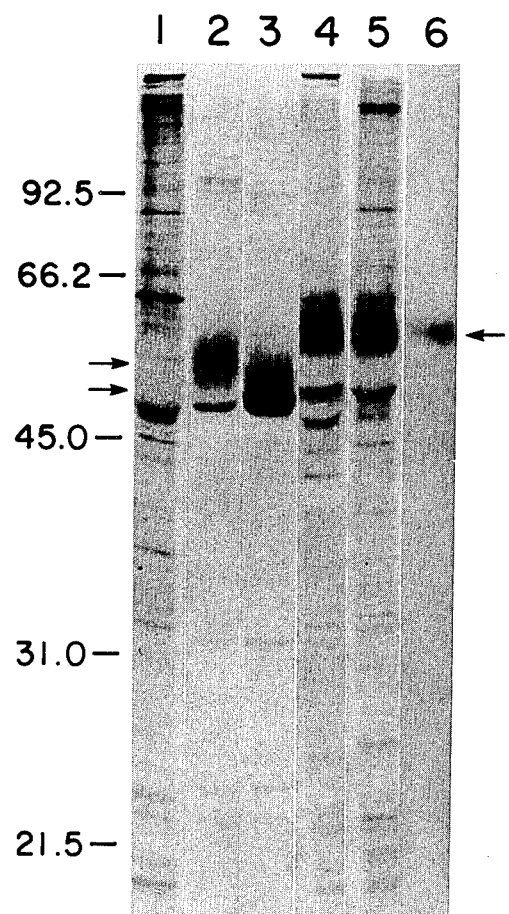
FIG. 5 shows radioimmunoprecipitations of cloned gD from the gD cell line hereof and native gD from HSV-1 infected human cells.

FIG. 5A compares autoradiographs obtained with the gD12 cell line and HSV-1 infected cells: control immunoprecipitation from the gD12 cell lysate with normal rabbit serum (lane 1); immunoprecipitation of native gD grown in HEL cells (lane 2) and A549 cells (lane 3) with the monoclonal anti-gD antibody, 55-S (41); immunoprecipitation of cloned gD from the gD12 cell lysate with polyclonal rabbit antibodies (Dako Corp.) to HSV-1 (lane 4), and the monoclonal antibody, 55-S (lane 5); immunoprecipitation of cloned gD from the gD12 cells metabolically labeled with $^{3}$H-glucosamine with polyclonal rabbit anti-HSV-1 antibodies (lane 6).

It is seen (lanes 4 and 5) that a diffuse band of 59-60 kd was specifically precipitated from the gD12 cell line using either rabbit anti-HSV-1 antibodies or the monoclonal anti-gD antibody, 55-S, specific for the HSV-1 protein (41). This molecular weight agrees well with that reported for gD isolated from HSV-1 infected KB cells (42). It is seen that the same monoclonal antibody precipitated proteins of similar but different molecular weights from HSV-1 infected human cell lines. The major product precipitated from the A549 human lung carcinoma cell line (lane 2) was 53 kd and that precipitated from the human embryonic lung cell line (HEL) was 56 kd (lane 3). Previous studies (43) have shown that the molecular weight of HSV glycoproteins varies depending on the host cell and that these difference are due to differences in glycosylation. To determine whether the gD protein produced in CHO cells was, in fact, glycosylated, the cells were metabolically labeled with $^{3}$H-glucosamine. Because bands of identical molecular weights (lanes 5 and 6) were precipitated after metabolic labeling with $^{35}$S-methionine or $^{3}$H-glucosamine, we concluded that the gD protein produced in CHO cells is glycosylated.

The human cell lines A549 (ATCC CCL 185) and HEL 299 (ATCC CCL 137) were grown to confluence in 3.5 cm tissue culture dishes and infected with HSV-1 at multiplicity of 10 pfu per cell. Virus infected cells were labeled by a method similar to that described by Cohen et al. (44). 4 hr after infection the medium was removed and the cells were washed once with fresh medium (Dulbecco's modified Eagle's medium) and once with phosphate-buffered saline (PBS). Fresh medium containing one-tenth the normal concentration of methionine was then added to the cells along with $^{35}$S-methionine (Amersham, International) to a final concentration of 75 μCi per ml of medium. The cells were grown an additional 20 hr and then harvested by treatment of washed cells with PBS containing EDTA (0.02 percent). Viral proteins were solubilized in lysis buffer consisting of PBS, 3 percent NP-40, 1 percent bovine serum albumin, $5 \times 10^{-5}$M phenylmethylsulfonyl fluoride, and 0.017 TIU/ml of apoprotinin. The resultant lysate was clarified by centrifugation at 12,000×g in a microcentrifuge. For immunoprecipitation reactions the cell or virus lysates were diluted 3-fold with phosphate buffered saline, mixed with 2-5 μl of the appropriate antiserum and incubated for 30 min at 4° C. Antibody-antigen complexes were removed from the reaction medium by the addition of 25 μl of a 10 percent solution fixed S. aureus (Kessler (40a)) and were precipitated by centrifugation at 12,000×g for 30 s. The S. aureus cells were then washed 3 times with wash buffer (PBS, 1 percent NP-40, 0.3 percent sodium dodecyl sulfate), and the cells suspended in 20 μl of polyacrylamide gel sampler buffer (10 percent glycerol, 5 percent 2-mercaptoethanol, 0.0625 M in pH 6.8 Tris buffer, 0.01 percent bromophenol blue) and incubated at 90° C. for 3 min. After centrifugation (12,000×g) for 30 s the supernatants were applied to 10 percent polyacrylamide slab gels (45).

Figure 5B:
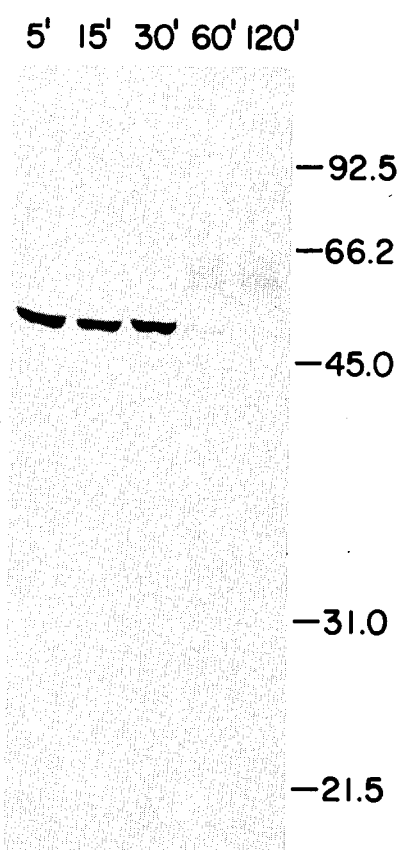

To further explore the post-translational processing of cloned gD, pulse-chase studies were conducted. FIG. 5B shows immunoprecipitation of cloned gD from gD-12 cells with rabbit anti-HSV-1 antibodies (Dako, Corp.) at various times after pulse labeling with $^{35}$S- methionine. FIG. 5B shows a pulse labelling of the gD12 cells. In these studies, cells were grown to confluence in 10 cm tissue culture dishes and labeled with $^{35}$S-methionine as described above with the exception that the labeling reaction was carried out for 15 min. on ice, the cells washed 3 times with fresh medium, and then returned to the incubator and incubated at 37° C. for various times. The reactions were terminated by washing the cells in cold phosphate-buffered saline and solubilizing the cells as described above. Proteins were immunoprecipitated at the following times after pulse labeling: lane 1, 5 min; lane 2, 15 min; lane 3, 30 min; lane 4, 60 min; lane 5, 120 min. The precursor form of gD with a molecular weight of 51 kd was specifically precipitated from the gD12 cell line 5 min after a pulse with $^{35}$S-methionine, and this precursor chased into the higher molecular weight form (59 kd) after approximately 60 min. From these studies we estimate the half-time for this post-translational event to be approximately 45 min. The precursor-product relationship between the 51 kd band and 59 kd band closely resembles that reported for virus produced gD (14,42,46,47) and the kinetics of this process are similar to those described by Cohen et al. (42). In virus infected cells the difference in molecular weights between the precursor and the product has been attributed to both N-linked and O-linked oligosaccharides (48).

Figure 4A:
FIG. 4 shows the result of labeling of gD12 cells with human antibodies against HSV, (A) being a visualization with phase contrast optics, (B) a fluorescence image of the same cells.
Figure 4B:

To determine whether gD was exported to the cell surface, indirect immunofluorescence studies were conducted. In these studies rabbit, mouse, and human anti-HSV antibodies were reacted with unifixed cells under conditions which do not permiablize the cell membrane (49). gD12 cells and the parental CHO cells (1:1 ratio) were plated onto glass coverslips (2.2×2.2 cm) and grown until the cells were approximately 60 percent confluent. Human serum known to contain antibodies to HSV-1 (50) was diluted forty-fold with phosphate buffered saline (PBS) and 100 μl was pipetted onto washed cells and was incubated for 30 min. at room temperature in a humidified chamber. The cells were immersed 3 times in PBS to wash away unbound antibody and then were incubated with 100 μl of 20-fold diluted tetramethylrhodamine isothiocyanate-labeled goat anti-human IgG antibodies (Cappel Laboratories) for an additional 30 min. The unbound labeled antibody was washed away with PBS and the cells were dehydrated in ice cold 50 percent ethanol and 100 percent ethanol and rehydrated with glycerol on a microscope slide (49). The cells were then viewed under phase-contrast and fluorescence optics in fluorescence microscope (Zeiss). FIG. 4 shows: A, gD12 and CHO cells viewed visualized with phase contrast optics; B, fluorescence image of the same cells as in A. Comparison of the phase-contrast images with the fluorescence images (FIG. 4) showed that the gD12 cells were heavily labeled, while the parental CHO cells bound little or no labeled antibody. In control experiments with normal mouse sera, normal rabbit sera, or human sera knows to be negative for HSV antibodies, no specific labeling of the cells could be detected. These studies suggested that the gD was exported to the cell surface. Experiments with CHO and gD12 cells fixed prior to labeling with agents known to permiablize the cell membrane (methanol or acetone) gave a different labeling pattern. In these studies we observed heavy perinuclear labeling of the gD12 cells with anti-HSV-1 antibodies, and no specific labeling of the CHO cells.

In order to determine whether gD12 cells expressed antigenic determinants relevant to human HSV-1 and HSV-2 infections, the binding of antibodies from individuals known to possess anti-HSV-1 or anti-HSV-2 antibodies (50) was examined. Radioimmunoprecipitation of lysates from metabolically labeled gD12 cells gave results comparable to those obtained with rodent anti-HSV sera (FIG. 5). Similarly, human anti-HSV-1 sera gave specific labeling of gD12 cells in an indirect immunofluorescence assay (FIG. 4) and did not label the parental CHO cell line. Taken together, the results obtained with various rodent anti-HSV-1 and HSV-2 antisera, monoclonal anti-gD antibodies and human anti-HSV antisera provide evidence that gD expressed on the surface of gD12 cells possesses a number of antigenic determinants in common with the native virus and that the structure of these determinants is not dependent on interactions with other HSV-1 proteins. The fact that one of the monoclonal antibodies tested (1-S) is known to neutralize HSV-1 in vitro (41) and in vivo (51) demonstrates that the gD produced in CHO cells possesses at least one of the neutralizing antigenic determinants in common with the native virus.

EXAMPLE 2

This example illustrates the use of gD12 cells formed in Example 1 in a sandwich-type immuno-assay for quantitatively measuring the binding of anti-HSV antibodies to gD12 cells in an enzyme-linked immunosorption assay (ELISA) (52). In these studies gD12 cells and CHO cells were plated and chemically fixed into alternate wells of 96 well microtiter tissue culture plates. Various antisera known to possess antibodies to HSV were then serially diluted and allowed to react with the fixed cells (see reference 52). At the end of the assay, the absorbance in each well was measured and normal binding curves were constructed. The specific binding of antibodies to the gD12 cells was determined by subtracting the values obtained with the parental CHO cells from those obtained from the gD12 cells. Specific binding by high titer sera could be detected at dilutions of 1:10,000.

Figure 6:
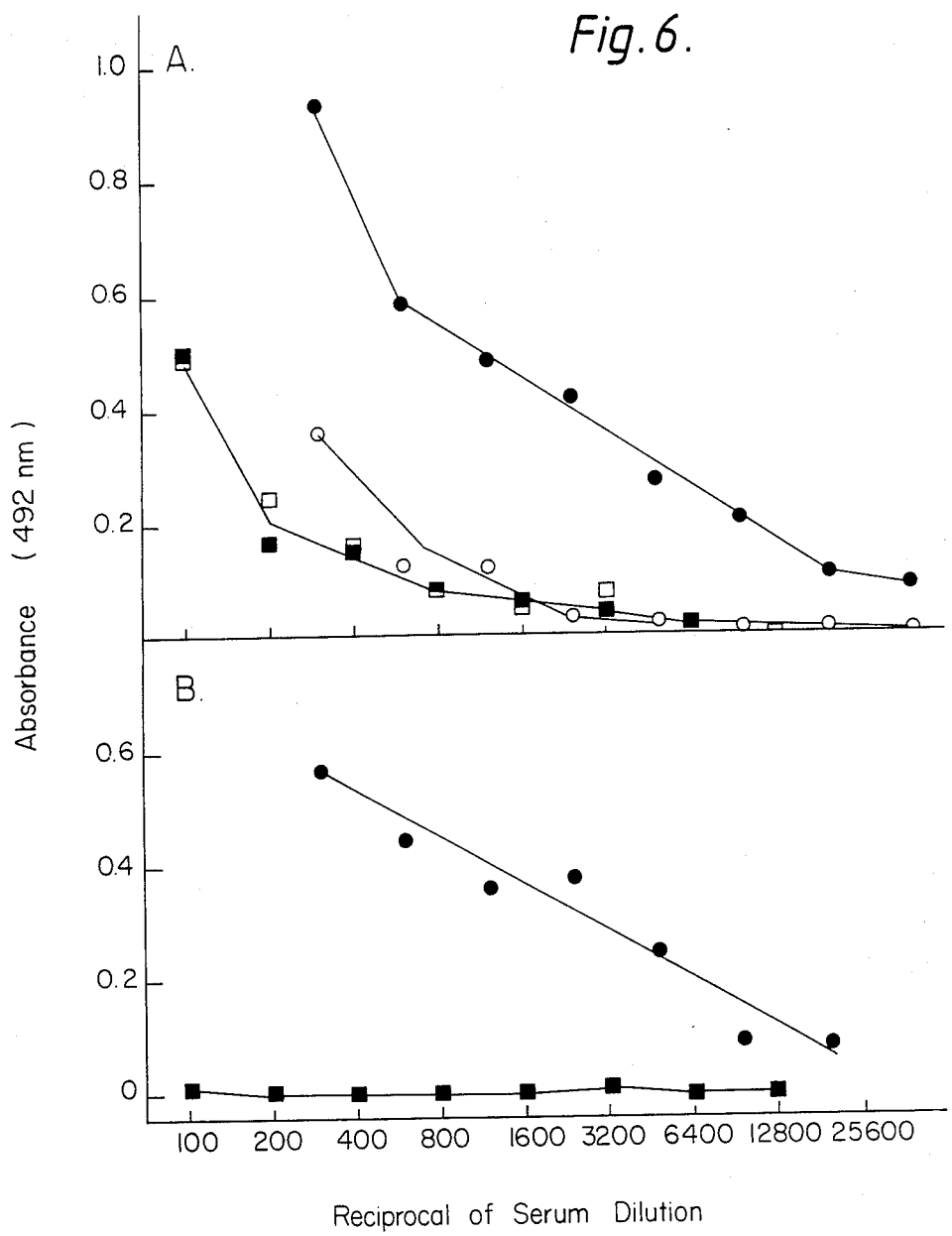
FIG. 6 shows the binding of human anti-HSV antibodies to gD12 cells and the parental CHO cell line.
Figure 7:
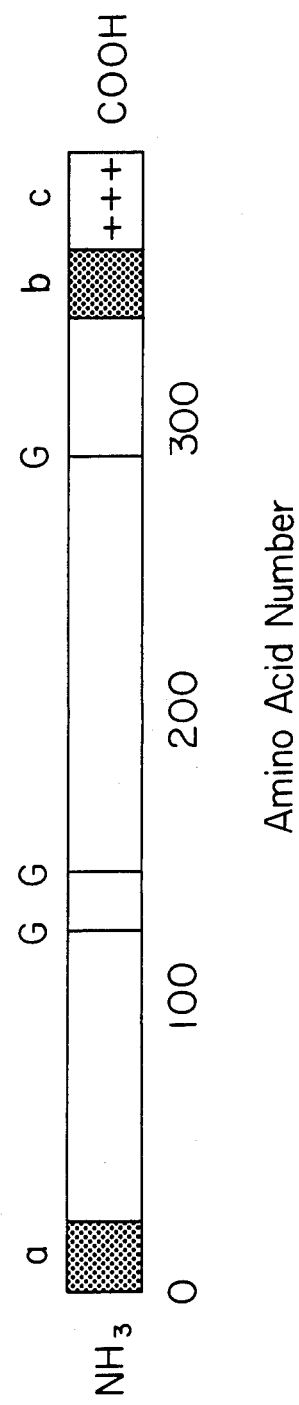
FIG. 7 is a schematic representation of HSV-1 gD protein and illustrates the locations of signal sequence and membrane-binding domain.

We compared serum titers determined using the gD12 cell ELISA assay with anti-HSV-1 and anti-HSV-2 titers determined by conventional methods. Human sera previously titered (50) against HSV by conventional assays, i.e., inhibition of hemagglutination (IHA) or complement fixation (CF), was serially diluted into wells of microtiter plates containing either gD12 cells or the parental CHO cell line and the binding of anti-gD antibodies was monitored in an ELISA assay. gD12 cells and the parental CHO cells were seeded into alternate wells of 96 well microtiter tissue culture plates (Falcon Labware) and were grown to confluence in F12 medium (GIBCO) containing 10 percent fetal bovine serum. The cells were washed three times with phosphate-buffered saline (PBS) and then were chemically fixed with 0.0625 percent glutaraldehyde in PBS. The cells were again washed three times with PBS and stored until needed at 4° in PBS containing 1 percent bovine serum albumin, 100 mM glycine 1 mM NaN$_3$. To measure anti-gD antibody titers, the cells were washed with PBS, and serially diluted antisera was allowed to react with the fixed cells (50 μl final volume) for 1 hr at room temperature. Unbound antibody was washed away and the cells were incubated with 50 μl of 1:2000 diluted goat anti-human IgG coupled to horseradish peroxidase (Tago, Inc.). The enzyme-linked antibody was allowed to react for one hour at room temperature, and the cells were then washed three times with PBS. After incubation, the peroxidase substrate, o-phenylene diamine, was added (200 μl) and the reaction was allowed to proceed for 10 min. The reaction was terminated by the addition of 2.5 M $H_2SO_4$ (50 μl) and the absorbance of the reaction medium from each well was determined with an automated plate-reading spectrophotometer (Titertek). In FIG. 6, the serum represented by the open and closed circles exhibited a HSV-1 CF titer of 128 and HSV-1 and HSV-2 IHA titers of 4096. The serum represented by open and closed squares exhibited a HSV-1 CF titer of <8 and HSV-1 and HSV-2 IHA titers of <8. A, closed circle and closed square indicate binding to gD12 cells; open circle and open square indicates binding to CHO cells. B, closed circle and closed square represents the specific binding to gD12 cells calculated by subtraction of the values in A. In FIG. 6 it can be seen that a serum with a high anti-HSV titer determined by conventional assays gave a high ELISA titer, while another serum with low anti-HSV titers gave no detectable binding in the gD12 ELISA.

The studies described demonstrate that stable cell lines constitutively express on their surface a transfected gene product which binds with antibodies generated by herpes virus infection.

A variety of transfection schemes are possible, of course, using a variety of selectable markers. For example, mouse L cells can be usefully transfected using a mutant dhfr gene as a selectable marker., The gD gene was transfected into such cells via a vector harboring such a marker.

A cell line such as gD12 may be used, inter alia, in the clinical diagnosis of HSV-1 and HSV-2 infections. The possibility of developing diagnostic reagents based upon clonal cell lines is appealing because it eliminates the need for the culture and containment of infectious agents while providing a stable, well defined reproducible source of antigen. When a cell-based diagnostic system is configured in the form of an ELISA, antibody determination can be performed in 2 hr or less and required less than 50 μl of serum.

EXAMPLE 3

This example illustrates the removal of the membrane from the expressed membrane-bound protein.

The foregoing description relates to the production of membrane-bound gD protein. However, as discussed above in relation to FIG. 2, analysis of the amino acid sequences of the gD protein of HSV-1 and HSV-2 identified in each case a hydrophobic/hydrophilic carboxyterminal membrane binding domain.

A Schematic Diagram of the HSV 1 Glycoprotein D (gD)

Hydrophobic (shaded) and hydrophilic (market +) regions of the protein were determined from the hydropathy analysis (31a) of the gD protein sequence derived from the gene sequence. Only those regions thought to be important for membrane localization and binding are shown. The functional domains are: (a) the signal sequence (33), (b) the hydrophobic transmembrane domain, and (c) the charged membrane anchor. The three putative N-linked glycosylation sites are shown by the letter G. The expression plasmid consisted of the pBR322 bacterial origin of replication and ampicillin resistance gene, a cDNA insert encoding the murine dihydrofolate reductase gene under the transcriptional control of the SV40 early promoter (53) and a HindIII-Hindf1 fragment which encodes the first 300 amino acids of gD under the transcriptional control of a second Sv40 early promoter. The HindIII site of this fragment lies 74 bp to the 5' side of the initiator methionine of the gD gene. The HindIII site of the SV-40 early region vector (36) lies 250 bp to the 3' side of the Goldberg-Hogness box of the SV40 promoter. The Hinf1 site (blunted with Klenow DNA polymerase and 4 deoxynucleotide triphosphates) is ligated to the Hpa1 site of the 3' nontranslated region of the hepatitis B virus surface antigen gene (36). This method is also useful for preparing a truncated HSV-2 gene.

The plasmid pgDtrunc.dhfr was constructed as follows: The 2.9 kilobase gD-containing Sac 1 fragment was isolated from the Bam H1 fragment cloned from the HSV 1 genome (see above) in the plasmid pFM3 (see above) cut with Sac 1. A 1.6 kilobase HindIII-Bst N1 fragment containing the entire gD gene was subloned into HindIII-Bst N1 digested pFM42 (EPO Application No. 68693). This plasmid was then cut with Hinf 1, blunted with Klenow DNA polymerase and four deoxynucleotide triphosphates, and then subsequently cut with HindIII. The 960 base pair HindIII-blunt Hinf 1 fragment containing the truncated gD gene was isolated and ligated to HindIII-Hpa1 digested pEH-Bal14. The resultant construction (pgDCos-trunc) contained the truncated gD gene with the hepatitis B surface antigen gene at its 3 prime end. A 2.3 kilobase HindIII-Bam H1 fragment containing the truncated gD gene was isolated from pgDCos-trunc. The 2.8 kilobase fragment containing the SV 40 origin-early promoter and the pBR322 ampicillin resistance gene and bacterial origin of replication were isolated from the plasmid pEHBal 14. The 2.1 kilobase fragment containing the murine dihydrofolate reductase cDNA clone under the transcriptional control of a second SV 40 early promoter was isolated from the plasmid pE348H-BVE400D22 (36). These three fragments were ligated together with T4 DNA ligase, and the resultant mixture was used to transform E. coli strain 294. Plasmid DNA from the resultant colonies was screened with Sac 2, and the correct construction pgDtrunc.dhfr (FIG. 8) was used for further transfection studies.

Plasmid pEHBal 14 was constructed by cleaving pE342ΔR1 (described below), an SV40-hepatitis chimera, with XbaI, which cleaves once in the coding region of the HBV surface antigen, and sequentially removing sequences surrounding this Xba I site by using nuclease Ba131. The plasmid was ligated in the presence of the synthetic oligonucleotide 5'-AGCTGAATTC, which joins the HBV DNA with a HindIII restriction site.

Resulting plasmids were screened for an Eco R1-Hind III fragment of ~150 b.p. pEHBal 14 was sequenced, which verified that a HindIII site had been placed at a point just upstream of where the HBsAg initiation codon is normally found. This construction thus places a unique HindIII site suitable for cloning at a position where a highly expressed protein (HBsAg) initiates translation. Any putative signals necessary for high expression of a protein should be present on this 5'leader sequence.

Plasmid pE342 which expresses HBV surface antigen (also referred to as pHBs348-E) has been described by Levinson et al, EPO Publication No. 0073656, Mar. 9, 1983, which is incorporated herein by reference. (Briefly, the origin of the Simian virus SV40 was isolated by digesting SV40 DNA with HindIII, and converting the HindIII ends to EcoRI ends by the addition of a converter (AGCTGAATTC)). This DNA was cut with PvuII, and RI linkers added. Following digestion with EcoRI, the 348 base-pair fragment spanning the origin was isolated by polyacrylamide gel electrophoresis and electroelution, and cloned in pBR322. Expression plasmid pHBs348-E was constructed by cloning the 1986 base-pair fragment resulting from EcoRI and BglII digestion of HBV (*Animal Virus Genetics*, (Ch. 5) Acad. Press, N.Y. (1980)) (which spans the gene encoding HBsAg) into the plasmid pML (Lusky et al., *Nature*, 293: 79 (1981)) at the EcoRI and BamHI sites. (pML is a derivative of pBR322 which has a deletion eliminating sequences which are inhibitory to plasmid replication in monkey cells). The resulting plasmid (pRI-Bgl) was then linearized with EcoRI, and the 348 base-pair fragment representing the SV40 origin region was introduced into the EcoRI site of pRI-Bgl. The origin fragment can insert in either orientation. Since this fragment encodes both the early and late SV40 promoters in addition to the origin of replication, HBV genes could be expressed under the control of either promoter depending on this orientation (pHBS348-E representing HBs expressed under control of the early promoter). pE342 is modified by partially digesting with Eco RI, filling in the cleaved site using Klenow DNA ploymerase I, and ligating the plasmid back together, thus removing the Eco RI site preceding the SV40 origin in pE342. The resulting plasmid is designated pE342ΔR1.

The resultant sequence creates a stop codon (TAA) immediately after amino acid 300 of the gD gene. The transcription termination and polyadenylation sites for the truncated gD gene transcript are encoded by the 3' untranslated region of the hepatitis B surface antigen gene (36).

Figure 9:
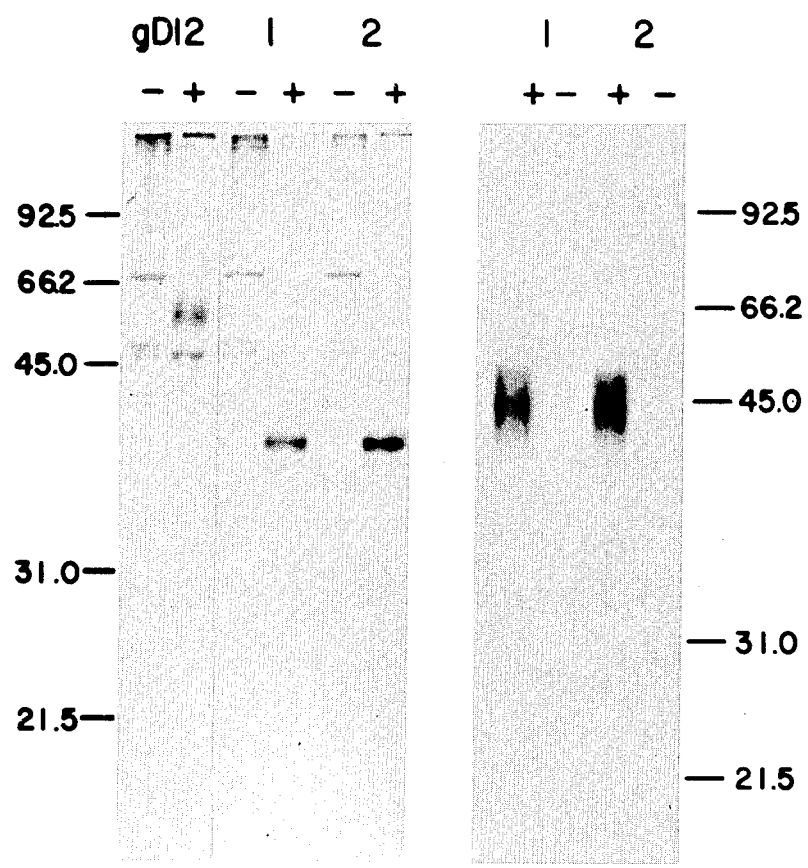
FIG. 9 shows radioimmunoprecipitations from the gD10.2 cell line hereof.

The resulting vector was transfected (40) into a dhfr$^-$ CHO cell line (39), and a suitable clone gG10.2 selected which produced the truncated gD protein and secreted it into the surrounding medium. The protein was extracted from the medium and the cells were tested for immunogenic activity. FIG. 9 shows the results of immunoprecipita- tions of intra- and extra-cellular $^{35}$S-methionine-labelled extracts.

Radioimmunoprecipitation of cell associated- and secreted-forms of gD. Cells were grown in Ham's F12 medium (Gibco) supplemented with 7 percent commercially dialyzed fetal bovine serum (Gibco), penicillin (100 u/ml), and streptomycin (100 u/ml). When the cultures were approximately 80 percent confluent, the medium was removed, the cells were washed twice with phosphate buffered saline (PBS), and labeling medium (Dulbecco's modified Eagle's medium containing one-tenth the normal concentration of methionine) was added to a final concentration of 0.05 ml/cm2. $^{35}$S-methionine (SJ.204, Amersham Int.) was added to a final concentration of 50–75 uCi/ml and the cells were grown for an additional 18–20 hr. After labeling, the medium was harvested and the cells were washed twice in PBS, and removed from the culture dish by treatment with PBS containing 0.02 percent EDTA. The cells were then solubilized in lysis buffer consisting of: PBS, 3 percent NP-40, 0.1 percent bovine serum albumin, $5 \times 5^{-5}$ M phenylmethylsulfonyl fluoride, and 0.017 TIU/ml of apoprotinin and the resultant lysate was clarified by centrifugation at $12,000 \times g$. For immunoprecipitation reactions cell lysates were diluted 3-fold with PBS and aliqouts (typically 180 μl) were mixed with 2-5 μl of antisera and incubated at 4° C. for 30 min. To immunoprecipitate the secreted form of gD, 500 μl of conditioned medium was incubated with 2 μl of antisera for 30 min at 4° C. Immune complexes were then adsorbed to fixed S. aureus cells by the method of Kessler (40a) and were precipitated by centrifugation at $12,000 \times g$ for 30 s. The S. aureus cells were then washed 3 times with wash buffer (PBS, 1 percent NP-40, 0.3 percent sodium dodecyl sulfate), and the immune complexes were eluted with 20 μl of polyacrylamide gel sample buffer (62.5 mM Tris-HCl buffer, pH 6.8 containing 10 percent glycerol, 5 percent 2-mercaptoethanol, 0.01 percent bromophenol blue) at 90° C. for 3 min. After centrifugation for 30 s the supernatants were applied to 10 percent polyacrylamide slab gels according to the method of Laemmli (45). A, immunoprecipitation of full length membrane bound gD from the gD12 cell line. B, immunoprecipitation of the cell associated form of the truncated gD from lysates of two independently derived cell lines (1 and 2). C, immunoprecipitation of the truncated gD from the culture supernatants of the two cell lines shown in B. (−), indicates control rabbit antiserum; (+), indicates rabbit anti-HSV-1 antiserum (Dako Corp.)

As can be seen, evident are an intracellular form of 35,000 Daltons and a secreted and apparently glycosylated extracellular gD protein.

Preparation of Truncated gD Used for Immunization gD10.2 cells were grown to confluence in polystyrene tissue culture roller bottles (Corning 25140) in F12 medium supplemented with 7 percent commercially dialyzed fetal calf serum, 50 μg/ml streptomycin, and 0.3 μg glutamine. After reaching confluence the medium was removed and the cells were washed three times in the same medium lacking fetal calf serum and supplemented with 2 mg/ml Hepes buffer (serum free medium). The cells were then grown 3-4 days in serum free medium and the conditioned medium was then harvested and stored at −20° C. The medium was thawed at 37° C. and centrifuged at 5000 rpm for 20 min. in a Sorvall GS-3 rotor. After centrifugation the pellet was discarded and the supernatant was concentrated in an ultrafiltration apparatus (Amicon) equipped with a YM-5 ultrafiltration membrane. The resultant preparation was concentrated approximately 150-fold relative to the starting material and contained approximately 8 mg of protein per liter. The preparation was then dialyzed extensively against phosphate buffered saline (PBS) and used for immunization without further purification.

The advantages of using the truncated protein for diagnostic applications is that, being secreted into the extracellular medium, it is contaminated with far fewer proteins than would be found in a whole-cell preparation.

It will be noted that the present invention uses a permanent cell line to produce the protein. Upon transfection the vector is incorporated into the genome of the cell line and can produce the protein without cell lysis. The cell line can thus be used for continuous production of the protein, especially in the truncated form which is secreted from the cell. For example, the cells expressing truncated protein can be continuously used in a perfusion system by constantly removing antigen-rich medium from the cells and replacing it with fresh medium.

The particular cell line used here was a CHO line deficient in dhfr production, transfected with a vector containing a dhfr marker. By exposing the cell line to methotrexate (Mtx) under suitable conditions (54) the dhfr production and hence the linked gD protein production can be amplified. Three cell lines derived by transfection of the truncated gD gene into dhfr−CHO cells were plated in parallel, labeled with $^{35}$S-methionine, and immunoprecipitated as described in FIG. 2. Lanes 1 and 2 indicate the amount of secreted gD immunoprecipitated from 500 μl of culture medium conditioned by two independently isolated cell lines before selection with methotrexate. Lane 3 indicates the amount of truncated gD immunoprecipitated from an equal volume of culture medium from a cell line (gD10.2.2) selected for growth in 250 nM methotrexate. Rabbit anti-HSV-1 antibodies (Dako Corp.) were used for the immunoprecipitations shown in lanes 1-3. Lane 4 represents a control immunoprecipitation of 500 μl of medium conditioned by the gD10.2.2 cell line with normal rabbit serum.

Figure 10:
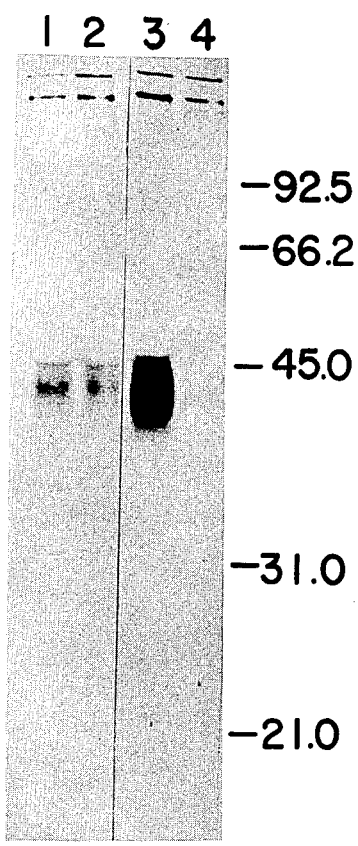
FIG. 10 shows radioimmunoprecipitations from preamplified and amplified gD10.2 cell lines.
Figure 11:
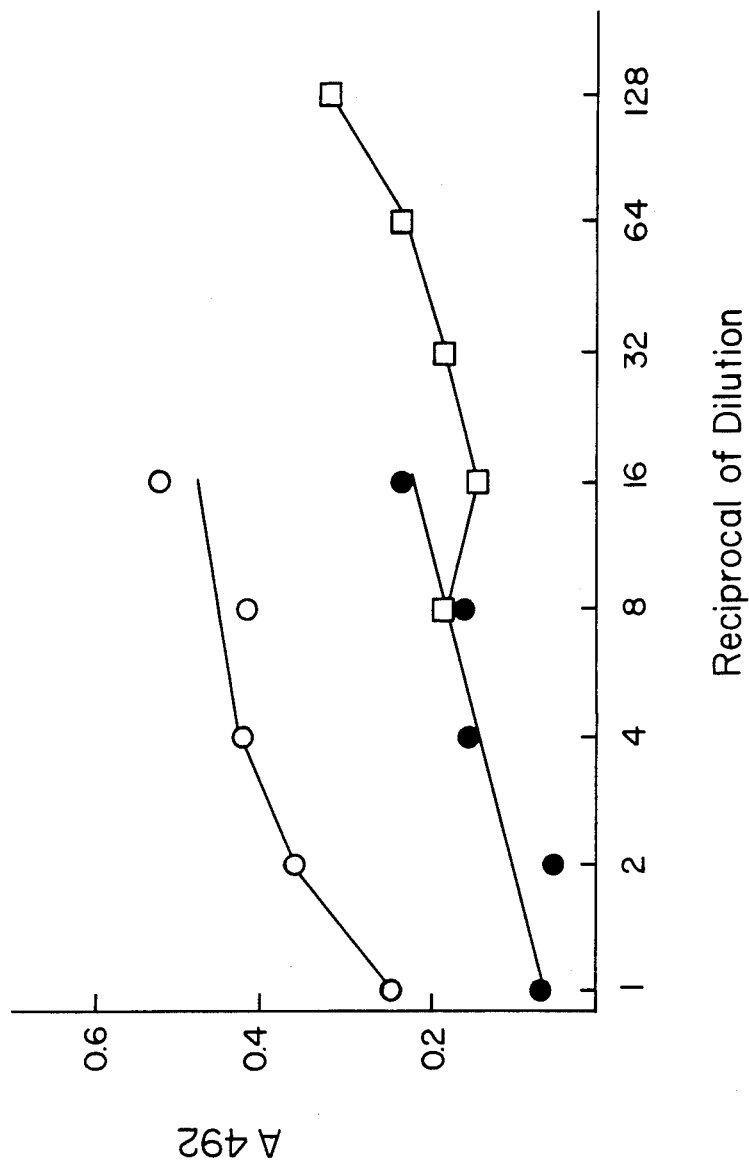
FIG. 11 demonstrates the degree of amplification achieved with the Mtx amplified gD10.2 cell line.

To quantitate the relative amounts of truncated gD secreted into the culture medium by cell lines before and after selection in methotrexate, a competitive ELISA assay was performed. gD12 cells expressing a membrane-bound form of gD were plated out and fixed with glutaraldehyde to the surface of 96 well microtiter plates as previously described. Conditioned medium from various cell lines known to produce the truncated gD was serially diluted across the microtiter plate and was incubated with a fixed quantity (2 μl) of rabbit anti-HSV-1 antibody (Dako Corp) for 1 hr and 20° C. Unbound antibody and soluble truncated gD-antibody complexes were removed by washing each well 3 times with PBS. Horseradish peroxidase coupled to goat anti-rabbit IgG was then reacted with the fixed cells for 1 hr at 20° C. and unbound antibody was removed by washing 3 times with PBS. The colorometric substrate, OPD (o-phenylene diamine), was then added to each well and allowed to react with the bound horseradish peroxidase-antibody complexes for 15 min. The reaction was terminated by the addition of sulfuric acid to a final concentration of 0.25 N. The absorbance of the OPD in each well was determined with the use of an automated microtiter plate scanner (Titertek multiskan) and dilution curves were plotted. The binding of anti-HSV-1 antibodies to the parental CHO line was used to measure the extent of nonspecific binding at each dilution. The amount of truncated gD in each culture supernatant was inversely proportional to the amount of absorbance in each well. Open circle, binding of anti-HSV-1 antibodies to gD12 cells in the presence of medium conditioned by cells secreting truncated gD before amplification with methotrexate. Closed circle, binding of anti-HSV-1 antibodies to gD12 cells in the presence of medium from gD10.2.2 cells selected for growth in 250 nM methotrexate. Open square, binding of anti-HSV-1 antibodies to gD12 cells in the presence of 100-fold concentrated medium from unamplified cells secreting truncated gD. This procedure was carried out on the gD10.2 cell line to produce an amplified cell line gD10.2.2 which was capable of growth in 250 nM Mtx and which secreted approximately 20-fold more truncated gD into the culture medium than the parental gD10.2 cell line (see FIGS. 10 and 11).

The dhfr marker/amplification system can be used with other cells which are able to acquire and stably incorporate foreign DNA.

The success of this invention in demonstrating that a truncated form of a membrane bound protein, lacking that part of the hydrophobic-hydrophilic carboxy-terminal region responsible for binding it to the membrane, can yet be immunogenic indicates that similar results can be expected with other immunogenic membrane bound protein, thus providing an improved source of vaccine against viruses, parasites and other pathogenic organisms.

In the foregoing example, the DNA of gD protein was truncated at residue 300 because there was a convenient restriction site there. This had the result that the carboxy-terminal hydrophobic/hydrophilic region was completely removed, as can be seen from the hydropathy plot of FIG. 2; indeed an additional preceding region was removed from residue 301 to 332 without, apparently, destroying the immunogenic character of the protein. It would seem to follow, therefore, that with this protein, and probably with other immunogenic membrane bound proteins, the extent of truncation could be considerably less if desired, so long as it has the effect of removing the membrane binding character so that the protein is secreted into the surrounding medium.

EXAMPLE 4

Example 4 relates to an HSV-2 gC protein (formerly designated a gF protein).

Cells, Virus, and DNA Isolation

HSV-2 (strain G) was grown on HEp 2 cells after infecting the cell culture at an input multiplicity of 0.1 for 3 days at 33° C. in Dulbecco's Modified Eagles Medium containing 10 percent fetal bovine serum and antibiotics. HSV-2 DNA was isolated by proteinase K digestion followed by CsCl ultracentrifugation as described (23).

DNA Manipulations

Restriction enzymes, DNA polymerase Klenow fragment, T4 DNA ligase, and T4 polynucleotide kinase were purchased from Bethesda Research Labs and were used according to the suppliers directions.

Molecular Cloning of HSV-2 DNA Restriction Fragments

The EcoR1 "P" fragment, which corresponds to approximate map position ~0.650 of the HSV-2 genome, was isolated from EcoR1 digested HSV-2 DNA on 5 percent acrylamide gels. The isolated fragment was cloned into EcoR1 digested pUC9 (28). This plasmid was called pUC-R1P.

The pUC-R1P subclone was then used to localize a Sac1 fragment of the HSV-2 genome which contained the EcoR1 "P" fragment. Southern blot experiments (27) revealed that a 4.9 kb Sac1 fragment of HSV-2 contained the EcoR1 "P" fragment. This fragment was isolated on 0.7 percent agarose gels and was cloned into a pBR322-derived plasmid which contained a unique Sac1 site (55). This plasmid was called pBRSac1-"E". Further restriction enzyme analysis of pBRSac1-"E" demonstrated a 2.9 kb Sal1 fragment with sequences homologous to the EcoR1 "P" fragment which was subcloned into Sal1 digested pUC9 as described above. This plasmid was called pgC$_2$Sa12.9.

DNA Sequence Analysis of Cloned HSV-2 DNA

The majority of DNA sequences were determined using the dideoxy nucleotide chain termination technique. Various fragments were subcloned into the replicative form of the m13 phage vectors mp7, mp8, and mp9, and the DNA sequence was determined as described previously (29). In some cases, fragments were $^{32}$P-labelled at their 5' ends with $\gamma^{32}$P-ATP and T4 polynucleotide kinase and the DNA sequence of the fragment was determined by using the chemical degradation method (56). Computer-assisted analysis of DNA and protein sequence data was performed using the HOM program (57). The hydropathy of the deduced amino acid sequences was analyzed using a width of 12 amino acids and a jump of 1 (31a).

Southern Blot Analysis of HSV-2 DNA

Restriction endonuclease digested HSV-2 DNA and plasmid DNA were fractionated on 1.5 percent agarose gels and blotted onto nitrocellulose using standard procedures. The single-stranded ends of the Sac2 fragment, marked with a star in FIG. 12, were filled in with the Klenow fragment of DNA polymerase 1, and the resultant blunt-ended fragment was ligated to Sma1 digested m13mp7 replicative form (29) with T4 DNA ligase. The single-stranded DNA prepared from this ligation and transfection was used as a template for the synthesis of $^{32}$P-labeled single-stranded probe DNA of high specific activity ($1 \times 10^9$ cpm/$\mu$g) using the Klenow fragment of DNA polymerase I. Hybridizations were performed using standard procedures (27,58).

RESULTS

Molecular Cloning of the gF Coding Region of the HSV-2 Genome

The strategy adopted for the isolation of the gF gene of HSV-2 was based on the assumption that this gene was colinear with the HSV-1 gC gene. This assumption was supported by the recent finding that a 75,000 dalton glycoprotein, gF, with antigenic relatedness to HSV-1 glycoprotein C is found in HSV-2 and that the gene for this protein is approximately colinear with the HSV-1 gC gene (22d,59). In addition, the isolation of a monoclonal antibody which binds to both HSV-1 gC and HSV-2 gF further suggested that these two proteins may be homologous to each other (22f). It was thus reasoned that DNA sequence analysis of the HSV-2 genomic region which is colinear with the HSV-1 gC gene would result in the derivation of protein sequence information which would localize the HSV-2 gF gene.

Figure 12:
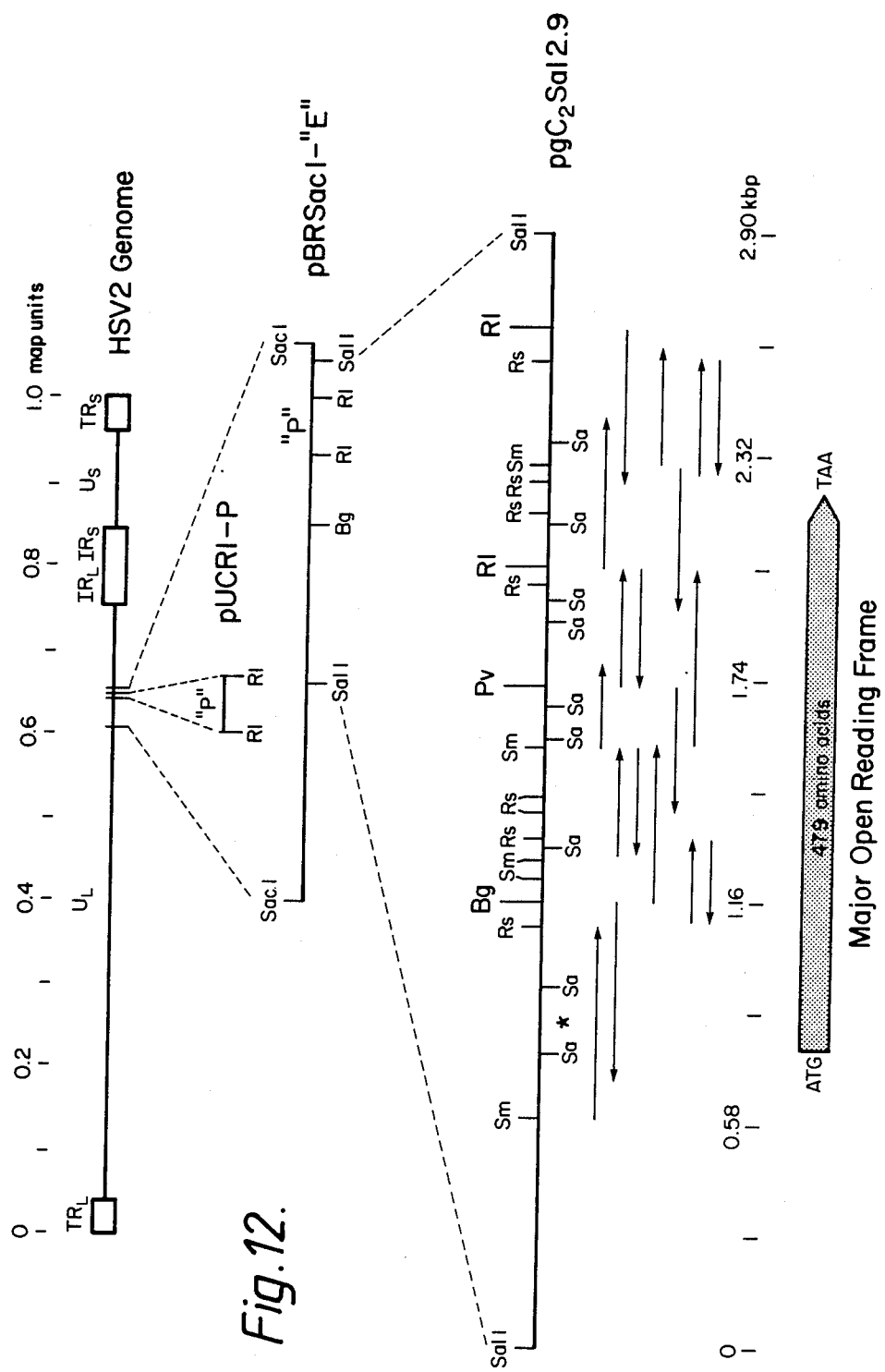
FIG. 12 shows the fragments of pgC$_2$Sa12.9 which were subjected to DNA sequence analysis.

The 600 basepair EcoR1 "P" fragment of the HSV-2 genome has been shown to map at position ~0.650 (12). This region is approximately colinear with the known coding region of the HSV-1 gC gene which maps between approximately 0.630 and 0.640 of the HSV-1 genome (59). This fragment was isolated from an EcoR1 digest of HSV-2 DNA, cloned in the plasmid pUC9 (28), and its DNA sequence was determined (29,56). Comparison of the resultant sequence with the HSV-1 gC sequence (59) revealed a remarkable degree of sequence homology between the EcoR1 "P" fragment and the 3' end of the HSV-1 gC coding region. Thus, the EcoR1 "P" fragment was subsequently used as a probe to isolate the Sac1 restriction endonuclease fragment from HSV-2 genomic DNA that overlapped the EcoR1 "P" fragment sufficiently to include the remainder of the HSV-2 gene which was homologous to the HSV-1 gC gene. FIG. 12 illustrates the steps taken to isolate a 2.9 kb Sal1 fragment from the HSV-2 genome which contained the EcoR1 "P" fragment and which was used for subsequent DNA sequence analysis.

DNA Sequence Analysis of the EcoR1 "P" region of the HSV-2 Genome

The 4.3 kb Sac1 "E" fragment, which was isolated from the HSV-2 genome based upon its sequence homology to the EcoR1 "P" fragment, was further digested to give a 2.9 kb Sal1 fragment which was termed pgC$_2$Sal2.9. FIG. 12 illustrates the fragments from pgC$_2$Sa$_l$12.9 which were subjected to DNA sequence analysis using either the dideoxy-nucleotide sequencing procedure (29) or the chemical degradation procedure (56). In addition, this figure shows the position of the EcoR1 "P" fragment within the pgC$_2$Sa12.9 as well as the position of a BglII site which corresponds to the right hand end of the BglII "N" fragment at position ~0.628 of the HSV-2 genome (12).

Specifically FIG. 12 shows the cloning of pgC$_2$Sa12.9, the HSV-2 region which maps colinearly with HSV-1 gC. The region of the HSV-2 genome mapping from ~0.61–0.66 was cloned as a Sac1 fragment (pBRSac "E") using the 600 basepair EcoR1 "P" fragment as a probe. A Sal1 subclone of pBRSac "E", pgC$_2$sa12.9, was used for DNA sequence analysis. Arrows refer to the sequenced regions, and the location of a major 479 amino acid open reading frame derived from the sequence is illustrated. Various restriction sites are illustrated, including the Eco R1 sites which delineate the EcoR1 "P" fragment, and the Bg1 2 site which is found at the right end of the Bg12 "N" fragment (map position ~0.628) (26). The Sac2 fragment marked with a star (*) was used in Southern blotting experiments to investigate the deletion which appears in this region (see results). Other sites were used for DNA sequencing experiments. Sm; Sma1, Sa; Sac2, Rsa: Rs1, Bg; Bg12, Pv; Pvu2, R1; EcoR1.

FIG. 13 illustrates the DNA sequence obtained from pgC$_2$Sa12.9 compared with the DNA sequence of the HSV-1 gC region (59). The HSV1 gC region (HSV-1) and the sequence obtained from pgC$_2$Sa12.9 (HSV-2) were compared using the HOM program (57). Because various deletions were utilized to maximize sequence overlap, all positions, including spaces, have been numbered for clarity. Stars are placed over the non-matching nucleotides. The underlined "A" residue at position 43 of the HSV-1 sequence is the approximate transcriptional start site of the gC mRNA (59). "TATA" 1 and "TATA" 2 are the probable transcriptional control regions for the HSV-1 gC mRNA and the 730 base mRNA, respectively (59,60). The inserted T residue at position 1728 of the HSV-1 sequence was discovered by resequencing this region (M. Jackson, unpublished) and was found to introduce an in-phase stop codon at positions 1735–1737 which was homologous to the stop codon for the HSV-2 major open reading frame. The position of the 730 base mRNA initiation codon of HSV-1 is shown at position 2032–2034, as in the position of a second HSV-2 initiation codon at position 1975–1977.

Referring again to FIG. 13 the illustrated derived sequence of HSV-2 was compared with the DNA sequence of the gC gene region of HSV-1 (59) which showed an overall sequence homology between these two fragments was approximately 68 percent. However, certain regions of the sequence showed either a much higher or lower degree of sequence homology than others. For example, the sequences between positions 0 and 570 of the HSV-1 and HSV-2 sequences showed only 51 percent homology, while the region between position 570 and 1740 showed a much higher degree of sequence homology (80 percent). An additional highly homologous region (70 percent) was also found at the end of the two sequences from position 1975 to position 2419. In addition to the nucleotide sequence changes, the two genomes showed various deletions or insertions when compared to each other. The most notable was an 81 basepair region found at position 346-426 of the HSV-1 gC sequence which is missing from the HSV-2 genome. From this overall sequence comparison it appeared that there was a high degree of sequence homology between the HSV-1 gC region and the HSV-2 region sequenced here.

Frink et al. (59) have found that the 5' end of the 2,520 base mRNA encoding HSV-1 gC maps to the underlined A residue at position 43 of FIG. 13. In addition, they pointed out an AT-rich "TATA" box (60) sequence approximately 22 basepairs 5' to this residue. Comparison of the two sequences shown in FIG. 13 shows that the HSV-1 and HSV-2 sequences both contained the identical sequence, CGGGTATAAA, in this region. This sequence is identical to that reported previously by Whitton et al. (61), which is found to occur at the "TATA" box regions in many of the HSV-1 and HSV-2 sequences determined thus far. This conserved sequence is also followed by a G-rich region in both virus genomes. In addition to this putative transcriptional-control region, a second "TATA" box was found in both sequences at position 1845-1849 of FIG. 13. This second "TATA" box has been hypothesized to control the transcription of a 73 0 base mRNA in the HSV-1 genome (59). Both HSV-1 and HSV-2 contain this sequence surrounded by GC-rich flanking sequences, including a CGGGCG sequence which is similar to the CGGG sequence preceding the first "TATA" box. In addition, both genomes encode open reading frames 3' to the second "TATA" boxes, which will be discussed below.

In order to determine if the 81 basepair deletion described above was actually found in the HSV-2 genome or if it was an artifact of cloning or sequencing, Southern blot analysis of the HSV-2 genomic DNA and the cloned HSV-2 DNA was performed. A $^{32}$P-labeled probe was prepared from a Sac2 fragment (see fragment in FIG. 12) which spans the region missing the 81 nucleotides. If the HSV-2 genomic DNA is missing the 81 basepair, then a Sma1-Bg1II fragment spanning this region will be 576 basepairs, a Sma1 fragment will be 662 basepairs, and a Sac2 fragment will be 195 basepairs.

FIG. 14 illustrates Southern blot analysis of HSV-2 genomic DNA and pgC$_2$Sa12.9 DNA. The region spanning the 81 basepair region missing in the HSV-2 sequence shown in FIG. 13 (HSV-2 positions 346-426) was analyzed using the Sac2 fragment marked with a star in FIG. 12 which overlaps the deleted region. Lanes 1-3 are restriction digests of HSV-2 genomic DNA, and lanes 4-6 are restriction enzyme digests of pgC$_2$Sa12.9. The digested DNAs were electrophoresed on 1.5 percent agarose gels, denatured, blotted onto nitrocellulose, and probed with the $^{32}$P-labeled Sac2 fragment. (The arrow shows the position of the 564 base pair HindIII fragment of phage λ DNA.) Lanes 1,6; Sma1+Bg12: lanes 2,5; Sma1: Lanes 3,4; Sac2.

The results shown in FIG. 14 demonstrate that the predicted restriction sites surrounded the region missing the 81 basepairs in both the HSV-2 genomic DNA and the cloned HSV-2 DNA. In addition, the HSV-2 genomic fragments are the cloned fragments comigrated exactly, demonstrating that the deletion is not an artifact of cloning or sequencing.

Analysis of the Major Open Reading Frame Within the HSV-2 2.9 kb Sal1 Fragment

Analysis of the potential coding sequences within the 2.9 kb Sal1 DNA fragment of HSV-2 revealed an open reading frame of 479 amino acids which began with the methionine encoded at position 199-201 of the HSV-2 sequence shown in FIG. 13 and ended at the TAA termination codon at position 1735-1737 of the HSV-2 sequence in this figure. As can be seen from FIG. 13, both the HSV-1 gC protein and the HSV-2 open reading frame initiate at approximately the same position in the two sequences, relative to the "TATA" box homologies. In addition, while it initially appeared that the HSV-2 open reading frame found in this region terminated 12 codons before the HSV-1 gC gene, resequencing of the carboxy-terminal region of the gC gene sequence (M. Jackson, unpublished) of HSV-1 strain F revealed that the sequence reported by Frink et al. (59) was missing a thymidine nucleotide after position 1727 and that insertion of this residue resulted in a translated HSV-1 gC protein terminating at the same place as the HSV-2 open reading frame (1735-1737 of FIG. 13). Thus, when taking the various deletions and insertions into account, as illustrated in FIG. 13, the HSV-1 gC gene and the HSV-2 open reading frame show a very high degree of overlap.

FIG. 15 illustrates translation of the HSV-2 large open reading frame and comparison with the HSV-1 gC amino acid sequence. The single letter amino acid symbols were used. HSV-1 gC refers to the HSV-1 gC sequence, and HSV-2 gF refers to the HSV-2 open reading frame sequence. The proteins were compared using the HOM program, which maximized homologies by inserting gaps where necessary (57). Stars are placed over non-homologous amino acids. Putative N-linked glycosylation sites (NXS or NXT) (62) are shaded, and cysteine residues (C) are boxed. Only amino acids, and not spaces are numbered. 15B illustrates translation of the second HSV-2 open reading frame and comparison with the HSV-1 730 base mRNA protein. 730 ORF HSV-2 is the incomplete amino acid sequence of the second HSV-2 open reading frame from positions 1975-2406 of the HSV-2 sequence shown in FIG. 13. 730 ORF HSV-1 is the amino acid sequence derived for the protein encoded by the 730 base mRNA of HSV-1 (59). Conserved amino acid changes, with respect to charge, are marked (C) and nonconserved changes, with respect to charge, are marked (N) in both FIG. 4A and 4B.

FIG. 15 illustrates the high degree of sequence homology between the HSV-1 gC gene and the 479 amino acid HSV-2 open reading frame. The first 19 amino acids contain approximately 80 percent sequence homology with the changes in the first 25 amino acids being all conservative with respect to charge. From residue 124 of HSV-1 gC (residue 90 of the HSV-2 sequence) to the end of both proteins there is about 74 percent sequence homology with 75 percent of the amino acid changes being conservative with respect to charge. Five putative N-linked glycosylation sites (NXS or NXT (62)) are conserved between the two proteins, and all 7 cysteine residues are located in homologous positions relative to the C-terminus. In addition to the overall conservation of sequences in the carboxy-terminal three-fourths of the proteins, there are also large regions of contiguous amino acid sequence homology up to 20 residues in length (i.e., position 385-405 of the HSV-1 sequence and 352-372 of the HSV-2 sequence). It may be concluded from this sequence comparison that the open reading frame in this region of the HSV-2 genome encodes a protein which is homologous to HSV-1 gC.

While the HSV-2 protein encoded in this region shows a remarkable degree of sequence homology to the HSV-1 gC sequence, there are several notable differences between the two sequences. The most striking difference is a deletion of 27 amino acids in the HSV-2 sequence which are found in the HSV-1 gC sequence from residues 50-76 (FIG. 15) and which corresponds to the 81 basepair deletion described above. In addition to this large deletion, both sequences show minor deletions of one or two amino acids. All of these deletions are found in the amino-terminal regions of the proteins. In addition to these deletions, there are a large number of amino acid changes in the amino-terminal region of the proteins which are clustered between residues 29-123 of the HSV-1 gC sequence (residues 31-90 of the HSV-2 sequence). Only 30 percent of the amino acids in this region are homologous, with much of this homology due to conserved proline residues. 43 percent of the amino acid substitutions found in this region are non-conservative with respect to charge. The only other regions which showed such a large number of changes are a carboxy-terminal hydrophobic domain (residues 476-496 of the HSV-1 sequence and 443-463 of the HSV-2 sequence) where the proteins are 55 percent homologous but where all the changes are conserved, uncharged, hydrophobic amino acids and the carboxy-termini of the proteins where the sequences are only 25 percent homologous, but where the overall amino acid composition is similar (residues 500-512 of the HSV-1 sequence and 467-479 of the HSV-2 sequence). While five of the putative N-linked glycosylation sites are conserved between the two proteins, the HSV-1 gC sequence contains two more sites than the HSV-2 sequence (9 versus 7 total). The HSV-1 gC sequence contains 2 M-linked glycosylation sites in the 27 amino acids deleted from the HSV-2 sequence, and an overlapping pair of sites between residues 109 and 112 of FIG. 15. The HSV-2 sequence contains two N-linked glycosylation sites not found in the HSV-1 sequence, one of which is proximal to the amino terminus.

In order to more fully examine the possible structural homologies between the HSV-1 and HSV-2 sequences, hydropathy analysis was performed (31a). FIG. 6 illustrates hydropathy analysis of the HSV-1 gC protein and the HSV-2 major open reading frame protein. The hydropathy of each protein was determined using the program of Hopp and Woods (31a). Hydrophobic regions are above the midline and hydrophilic regions are below the midline. Stretches of 12 amino acids were analyzed, and the average hydropathy was calculated. Putative asparagine-linked glycosylation sites (62) are marked (0). gC-1: HSV-1 gC protein hydropathy. gC-2 (gF): HSV-2 major open reading frame protein hydropathy.

Figure 16:
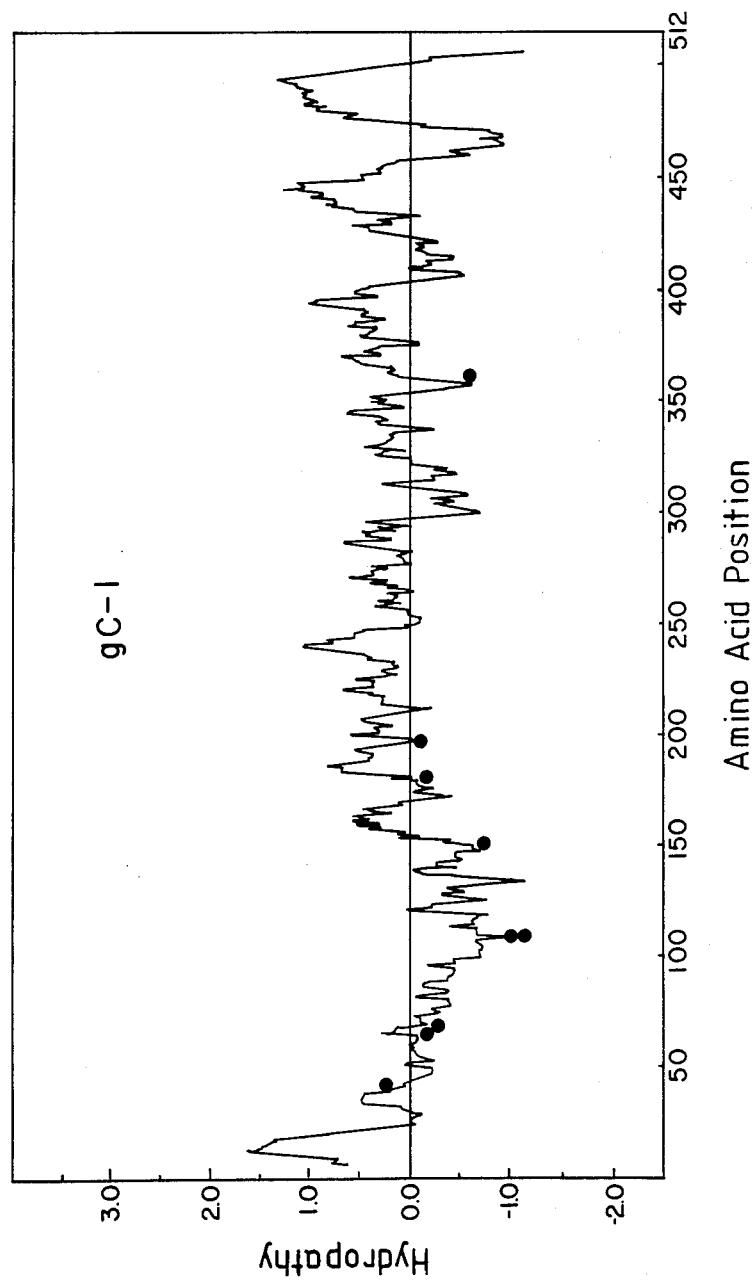
FIG. 16 illustrates hydropathy analysis of the HSV-1 gC protein and the HSV-2 major open reading frame protein.
Figure 16:
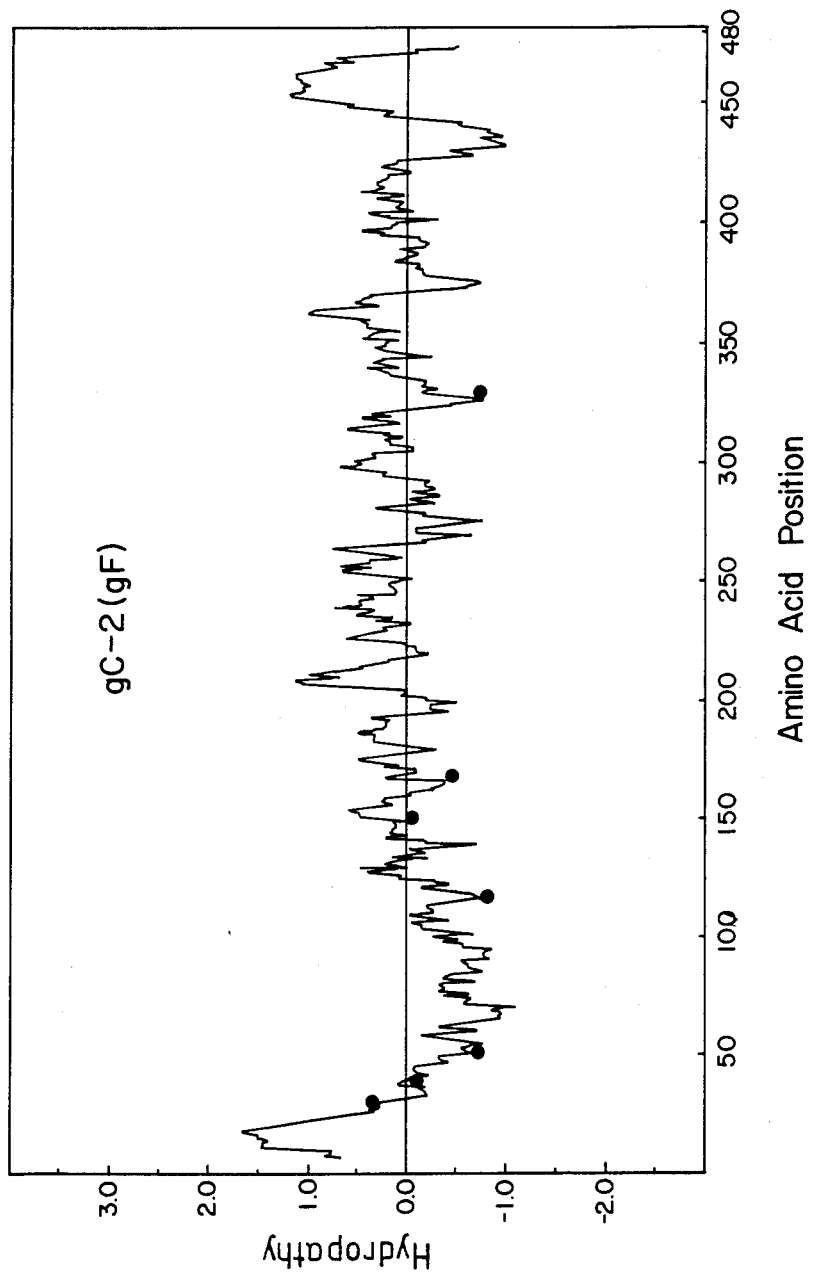

FIG. 16 shows that both proteins exhibited an extraordinary degree of structural homology based on the hydrophilic and hydrophobic properties of the amino acid sequences. Each show an N-terminal hydrophobic domain followed by a stretch of hydrophilic amino acids which contain either 6 of 9 total (HSV-1) or 3 of 7 total (HSV-2) putative N-linked glycosylation sites. The peaks and valleys which follow this hydrophilic region are very similar in both proteins, including the hydrophilic domain containing the final N-linked glycosylation site. The carboxy-termini of both proteins shows a very hydrophobic 20 residue region followed by hydrophilic carboxy-terminus. The 27 contiguous amino acids found exclusively in the HSV-1 gC protein appear to encode a relatively hydrophilic regions between residues 50-76 (FIG. 16). In conclusion, this analysis reveals that the hydrophatic features of both the HSV-1 gC and the HSV-2 protein are very similar and that the least conserved amino-terminal regions of the proteins are found in hydrophilic regions which have the potential to the highly glycosylated.

Analysis of the Second HSV-2 Open Reading Frame

Translation of the final 431 basepairs of the HSV-2 sequence shown in FIG. 2 (residues 1975-2406) revealed a second open reading frame of 105 amino acids. Although the sequence information reported here is insufficient to contain the entire HSV-2 second open reading frame, comparison of this sequence with the open reading frame encoded by the 730 base mRNA of HSV-1 reported by Frink et al. (10) also revealed a high degree of sequence homology. As can be seen if FIG. 4b, the two sequences showed 75 percent sequence homology in the overlapping regions, with about 90 percent of the amino acid changes being conservative with respect to charge. The major difference between the two sequences was a 19 amino acid N-terminal region which was found in the HSV-2, but not HSV-1 sequence. Thus, although the function of the protein encoded in this region is unknown, the proteins from HSV-1 and HSV-2 show a considerable degree of sequence homology.

DISCUSSION

The above results demonstrate that the HSV-2 genome encodes a colinearly mapping homologue of the HSV-1 glycoprotein C. The colinearity of the sequences found here is strengthened by the finding of a sequence 3' of the HSV-2 major open reading frame which apparently encodes a homologue of the HSV-1 730 base pair mRNA (10). Previous mapping of the HSV-2 gF gene (33), together with the properties described here for the major open reading frame in this region of the HSV-2 genome including several potential N-linked glycosylation sites and an apparent amino-terminal signal sequence (5) as well as a putative carboxy-terminal transmembrane domain (28) allow the conclusion that the HSV-2 protein described here is the glycoprotein, gF. In addition, the size of the translated HSV-2 protein (~52,000 daltons) is similar to that reported for the endoglycosidase H-treated, native size for HSV-2 gF (54,000 daltons) (22d). Finally, the large extent of amino acid sequence homology as well as the conservation of several potential N-linked glycosylation sites and of all 7 cysteine residues indicates structural homology between HSV-1 gC and HSV-2 gF. These results, then, strongly suggest that the HSV-1 gC protein and the HSV-2 protein are homologous to each other.

These results help explain previous results which demonstrated that the HSV-2 gF and HSV-1 gC proteins were mainly type-specific, but that they did have type-common determinants (17,22d,22f,43). Since several previous studies (17,18,43) demonstrated that these proteins induced predominantly type-specific antibodies, it is reasonable that the most antigenic regions of the proteins are found within the more divergent N-terminal sequences which follow the putative hydrophobic signal sequences. The hydrophilic nature of the divergent regions, along with their content of potential N-linked glycosylation sites (62), suggests that these regions would be located on the surface of the protein.

Exposure of these divergent sequences to the outside of the proteins may be responsible for the generation of type-specific antibodies directed against these divergent epitopes. However, type-common antibodies could likely also be generated by the more highly conserved carboxy-terminal three-fourths of the proteins, since hydrophilic regions conserved between gC and gF could be exposed to the outside of the proteins and may be, in one case, glycosylated (residues 363–366 of HSV-1 gC and 330–332 of HSV-2 gF). Thus, HSV-1 gC and HSV-2 gF share both type-specific and type-common determinants, but it appears that the type-specific determinants are more antigenic.

Although an explanation of the type-specific and type-common determinants of gC and gF is not known, it is possible that the proteins have at least two functions, one of which is important for the viability of both viruses, the type common domain, and one of which is specific for each virus type, the type-specific domain. While the function(s) of gC and gF is at present unknown, and while viable gC minus mutants of HSV-1 have been isolated in vitro (65), it is not clear that either gC or gF are indispensable to the viruses during in vivo infection of the human host and the establishment of latency. It is possible that at least some of the biological differences between HSV-1 and HSV-2, including predilection for site of infection and virulence, may be due to the marked structural differences between the amino-terminal regions of gC and gF. It may be concluded, even in the absence of any functional knowledge of these proteins, that different selective pressures must be operating on the divergent and conserved domains of gC and gF. Previous sequence comparison of the gD genes of HSV-1 and HSV-2 (58) demonstrated that the amino-terminal signal sequence (63) and the carboxy-terminal transmembrane domain (64) were able to tolerate a large number of mutations as long as the substituted amino acids were hydrophobic. The gC and gF sequence comparison demonstrates a similar finding in the carboxy-terminal, putative transmembrane domain (64) from residues 476–496 of gC and 443–463 of gF. The large number of heterologous hydrophobic substitutions in this region suggests that, as in gD, any amino acid which is lipid-soluble can be tolerated in this region. In contrast to gD, however, the amino-terminal signal sequences of gC and gF are highly homologous in the first 19 residues. Thus, either this region has an important conserved function other than direction of the glycoproteins into the rough endoplasmic reticulum (5), or there may be an overlapping gene or other functional sequence in this region of the genome which must be conserved (66).

Although insufficient HSV-2 sequence is presented here for a complete comparison, the region 5' to the start of HSV-1 gC mRNA transcription shows an identical CGGGTATAA sequence in both the HSV-1 and HSV-2 genomes. In addition, both sequences are followed by a G-rich region immediately preceding the start of transcription. Thus, as was previously found for the gD genes of HSV-1 and HSV-2, upstream sequence homologies exist between the two virus types which suggest the possibility that these regions are involved in transcriptional regulation of these genes. Interestingly, the second "TATA" box homology found in both virus genomes, which probably controls transcription of the 730 base mRNA (59,60), also shows a relatively high degree of sequence homology in HSV-1 and HSV2. These "TATA" boxes are preceded by CG-rich sequences, which are similar, but not identical, to those preceding the first "TATA" regions shown in FIG. 13, and they are both followed by a 14 basepair region showing ~80 percent sequence homology. The entire region of homology surrounding this region is only 33 basepairs with an overall sequence homology of ~75 percent. If this region is involved in transcriptional regulation of the 730 base mRNA, then it appears that a relatively short sequence may be sufficient for recognition by transcriptional regulatory elements.

In conclusion, the results demonstrate that the HSV-1 gC and HSV-2 gF glycoproteins are highly homologous, and that they encode type-common and type-specific domains. Since the two proteins do show significant sequence homology, and since they apparently map colinearly, we favor the proposal of Zezulak and Spear (22d) to rename HSV-2 gF and HSV-2 gC or gC-2. In addition, the sequencing data reported here opens the way for a functional analysis of the gC-1 and gC-2 proteins by the interchange of various type-specific regions between the two proteins in vitro and expression of the chimaeric sequences in mammalian cells (67) or by reincorporation of these regions back into the virus (68).

The cloned gC-2 glycoproteins may be expressed in a manner analogous to the expression of gD set forth in Example 1. A fragment of gC-2 which includes a sequence which is type-specific for gC-1, but which excludes the sequence which is type-common for gC-1 and gC-2, is highly useful as a diagnostic agent which distinguishes HSV-1 from HSV-2.

The references grouped in the following bibliography and respectively cited parenthetically by letter or number in the foregoing text, are hereby incorporated by reference.

BIBLIOGRAPHY

A. Jordan, et al., A.J.C.P. 467 (October 1981).
B. Kimmel, et al., J. Virol. 219 (1982).
1. Emtage, et al., Nature 283, 171 (1980); Davis, et al., Proc. Natl. Acad. Sci. (USA) 78, 5376 (1981); Weiland, et al., Nature 292, 851 (1981).
2. Kupper, et al. Nature 289, 555 (1981); Kleid et al. Science 214, 1125 (1981).
3. Charnay, et al, Nucleic Acids Research 7, 335 (1979); Valenzuela, et al., Nature 298, 347 (1982).
4. Rose, et al., Proc. Natl. Acad. Sci. (USA) 78, 6670 (1981).
5. Yelverton, et al., Science 219, 614 (1983).
6. Watson, et al., Science 218, 381 (1982).
7. Gething, et al., Nature 293, 620 (1981); Liu, et al., DNA 1, 213 (1982); Goodenow, et al., Science 215, 677 (1982); Goodenow, et al., Nature 300, 231 (1982); Crowley, et al., Molec. and Cell. Biol. 3, 44 (1983).
8. Rose, et al., Cell 30, 753 (1982).
9. Spear, P. G., (1980), Herpesviruses, p709–750, in H. A. Blough and J. M. Tiffaney (ed.), Cell Membranes and Viral Envelopes, Vol. 2., Academic Press, Inc., New York.
10. Balachandran, et al., J. Virol. 44, 344 (1982).
11. Norrild, Curr. Top. Microbiol Immunol. 90, 67 (1980).
12. Roizman, Cell 16, 481 (1979).
13. Baucke, et al., J. Virol. 32, 779 (1979).
14. Cohen, et al., J. Virol. 27, 172.
13. Eberle, et al., J. Virol. 36, 665 (1980).
16. Norrild, et al., J. Virol. 26, 712 (1978).
17. Powell, et al., Nature 249, 360 (1974).

18. Eberle, et al., *Infect. Immun.* 31, 1062 (1982).
19. Pereira, et al., *Infect. Immun.* 29, 724.
20. Sim, C., et al., *J. Gen. Virol.* 19, 217 (1973).
21. Showalter, et. al., *Infect. Immun.* 34, 684 (1982).
22. Eisenberg, et. al., *J. Virol.* 41, 1099.
22a. Para, et al., *J. Virol.* 41, 137 (1982).
22b. Balachandran, et al., *J. Virol.* 39, 438 (1982).
22c. Para, et al., *J. Virol.* 41, 137 (1982).
22d. Zezulak, et al., *J. Virol.* 47, 553 (1983).
22f. Zweig, et al., *J. Virol.* 47, 185 (1983).
23. Anderson, et al., *J. Virol.* 30, 805 (1979).
24. Lee, et al., *J. Virol.* 43, 41 (1982).
25. Murray, et al., *Mol. Genet.* 150, 53 (1977).
26. Benton, et al., *Science* 196, 180 (1977).
27. Southern, *J. Mol. Biol.* 98, 503 (1975).
28. Vieira, et al., *Gene* 19, 259 (1982).
29. Messing, et al., *Nuc. Acid. Res.* 9, 309 (1981).
30. Sanger, et al., *Proc. Natl. Acad. Sci. (USA)* 74, 5436 (1977).
31. *Atlas of Protein Sequence and Structure V.* 5, Supplement 2, 1976, M. O. Dayhoff, ed., The Biochemical Research Foundation, Spring, Maryland, p. 311.
31a. Hopp, et al., *Proc. Natl. Acad. Sci. (USA)* 78, 3824 (1981).
32. Watson, et al., *Nucl. Acid. Res.* 11, 1507 (1983).
33. Blobel, *Proc. Natl. Acad. Sci. (USA)* 77, 1746 (1980).
34. Rose, et al., *Proc. Natl. Acad. Sci. (USA)* 77, 3884 (1980).
35. Ruyechan, et al., *J. Virol.* 29, 677 (1979); Roizman, *Cell* 26, 481 (1979).
36. Simonsen, et al., *Proc. Natl. Acad. Sci. (USA)* 80, 2495 (1983).
37. Lusky, et al., *Nature* 293, 79 (1981).
38. Nunberg, et al., *Cell* 19, 355 (1980). 39. Urlaub, et al., *Proc. Natl. Acad. Sci. (USA)* 77, 4216 (1980).
40. Graham, et al., *Virol.* 52, 456, (1973).
40a. Kessler, J. *Immuno.* 115, 1617 (1975).
41. Showalter, et al., *Infect. and Immun.* 34, 684 (1981); Monoclonal anti-gD antibodies, 1-S and 55-S were kindly provided by Dr. Martin Zweig of the Laboratory of Molecular Oncology, National Cancer Institute, Frederick, Md. 21701.
42. Cohen, et al., *J. Virol.* 36, 429 (1980).
43. Pereira, et al., *Proc. Natl. Acad. Sci. (USA)* 78, 5202 (1981).
44. Cohen, et al., *J. Virol.* 27, 172 (1978).
45. Laemmli, *Nature* 227, 680 (1970).
46. Honess, et al., *J. Virol.* 16, 1308 (1975).
47. Spear, *J. Virol.* 17, 991 (1976).
48. Campadelli-Fiume, et al., *J. Virol.* 43, 1061 (1982); Johnson, et al., *Cell* 32, 987 (1983); Cohen, et al., *J. Virol.* 46, 679 (1983).
49. Bloch, *J. Cell. Biol.* 82, 629 (1979).
50. Human herpetic serum titered against HSV-1 and HSV-2 by inhibition of hemagglutination and complement fixation assays was kindly provided by Dr. John A. Stewart of the Centers for Disease Control, Atlanta, GA.
51. Rector, et al., *Infect. and Immun.* 38, 168 (1982).
52. Kennett, in *Monoclonal Antibodies,* K. Kerrett, T. McKearn, and B. Bechtel, eds. (Plenum Press, N.Y., 1980), pp. 376–377.
53. Fiers, et al., *Nature* 273, 113 (1978); Gluzman, *Cell* 23, 275 (1981).
54. Lee, et al., *Nature* 294, 228 (1981); Kaufman, et al., *Mol. and Cell. Biol.* 2, 1304 (1983); Kaufman, et al., *J. Mol. Biol.* 159, 601 (1982).
55. Kleid, et al., *Science* 214, 1125 (1981).
56. Maxam, et al., *Methods Enzymol.* 65, 499 (1980).
57. Dayhoff, M., Ed. Atlas of Protein Sequence and Structure Vol. 5, Supplement 2, National Biochemical Research Foundation, Silver Spring, Md., p. 311 (1976).
58. Lasky, et al., *DNA,* in press (1984).
59. Frink, et al., *J. Virol.* 45, 634 (1983).
60. McKnight, et al., *Science* 217, 316 (1982).
61. Whitton, et al., *Nucl. Acids Res.* 18, 6271 (1983).
62. Hubbard, et al., *Ann. Rev. Biochem.* 50, 555 (1983).
63. Blobel, *Proc. Natl. Acad. Sci. USA* 77, 1491 (1980).
64. Sabatini, et al., *J. Cell, Biol.* 92, 1 (1982).
65. Cassai, et al., *Intervirology* 6, 212 (1975).
66. Hall, et al., *J. Virol.* 43, 594 (1982).
67. Berman, et al., *Science* 222, 524 (1983).
68. Gibson, et al., *J. Virol.* 48, 396 (1983).

What is claimed is:

1. A diagnostic product comprising membrane-bound polypeptide having antigenic determinants capable of specifically binding complementary antibody to herpes simplex virus, said polypeptide being functionally associated with the membrane of a recombinant, stable, continuous cell line capable of its production.

2. The diagnostic product of claim 1 in which said polypeptide is a glycoprotein D of herpes simplex virus type 1 or type 2, and is capable of binding antibodies of herpes simplex virus type 1 and/or type 2.

3. The diagnostic product of claim 1 in which said polypeptide is a glycoprotein C of herpes simplex virus type 1 or type 2.

4. The diagnostic product of claim 3 in which said polypeptide comprises a fragment of glycoprotein C of herpes simplex virus type 2 and is capable of binding complementary antibodies to herpes simplex virus type 1 or type 2.

5. The diagnostic product of claim 3 in which the polypeptide comprises a fragment of glycoprotein C capable of binding complementary antibodies to herpes simplex virus type 2, but not herpes simplex virus type 1.

6. The diagnostic product of claim 1 bound to a solid surface.

7. The diagnostic product of claim 1 linked to a label.

8. The diagnostic product of claim 7 in which said label comprises an enzyme.

9. The diagnostic product of claim 1 in which said recombinant cell is mammalian.

10. The diagnostic product of any one of claims 1, 2 to 8, or 9 in a diagnostic test kit, together with a labeled anti-antibody capable of specifically binding said complementary antibody.

11. The diagnostic product of claim 10 together with unlabeled complementary antibody in said diagnostic test kit.

12. The diagnostic product of any one of claims 1, 2 to 7 or 8, together with labeled complementary antibody in a diagnostic test kit.

13. A diagnostic test kit comprising:
(a) a diagnostic product comprising a membrane-bound polypeptide with antigenic determinants capable of specifically binding complementary antibodies to herpes simplex virus, said polypeptide being formed in a recombinant, stable, continuous cell line; and
(b) a second component comprising either said complementary antibody or anti-antibody capable of specifically binding said complementary antibody.

14. The diagnostic test kit of claim 13 in which said diagnostic product is bound to a solid surface.

15. The diagnostic test kit of claim 13 in which said diagnostic product is linked to a label.

16. The diagnostic test kit of claim 13 in which said second components comprises labeled anti-antibody capable of specifically binding said complementary antibody.

17. The diagnostic test kit of claim 16 further comprising unlabeled complementary antibody.

18. The diagnostic test kit of claim 13 in which said second component comprises complementary antibody.

19. The diagnostic test kit of claim 13 in which said diagnostic product is a truncated, membrane-free derivative of a polypeptide, said derivative being devoid of a membrane-binding domain whereby the derivative is free of said membrane.

20. The diagnostic test kit of claim 19 in which the truncated polypeptide is formed by secretion from a recombinant eukaryotic host cell system capable of its production.

21. The diagnostic test kit of claim 13 in which the diagnostic product comprises a membrane-free derivative of the polypeptide in which the polypeptide first is formed functionally associated with a membrane of said recombinant, stable, continuous cell line and then dissolved free from said membrane.

22. The diagnostic test kit of claim 13 in which said diagnostic product comprises a glycoprotein of herpes simplex virus type 1 or type 2.

23. The diagnostic test kit of claim 22 in which said glycoprotein is capable of binding either herpes simplex virus type 1 or type 2, but not both.

24. The diagnostic test kit of claim 22 in which said glycoprotein is capable of binding complementary antibodies to either herpes simplex virus type 1 or type 2, but not both.

25. The diagnostic test kit of claim 22 in which said diagnostic product comprises a glycoprotein C of herpes simplex virus type 1 or type 2.

26. The diagnostic test kit of claim 25 in which said glycoprotein C is of herpes simplex virus type 2.

27. The diagnostic test kit of claim 26 in which said polypeptide comprises a fragment of herpes simplex virus type 2 capable of binding complementary antibodies to herpes simplex type 2, but not herpes simplex type 1.

28. A method for the detection of antibody contained in a biologically derived fluid sample comprising the steps of:
(a) contacting said fluid sample with the diagnostic product of claim 1 to bind the diagnostic product with complementary antibody in the fluid sample; and
(b) detecting the binding of step (a).

29. The method of claim 28 in which the binding of step (a) is also measured.

30. The method of claim 28 in which in step (a) said diagnostic reagent is bound to a solid surface, and said sample also is contacted with soluble labeled anti-antibody capable of specifically binding said complementary antibody, to cause said sample antibody to bond on said solid surface both to said diagnostic product and said labeled anti-antibody; said method further comprising prior to step (b) separating the solid surface from the solution containing unreacted, soluble labeled antibody; and wherein in step (b) the labeled anti-antibody is detected in either the solid phase or the separated solution.

31. The method of claim 29 in which in step (a) said diagnostic product is bound to a solid surface, and said sample also is contacted with soluble labeled antibody also capable of specifically binding said diagnostic product, to cause said sample antibody and labeled antibody to bind competitively to said diagnostic product on said solid surface; said method further comprising prior to step (b) separating the solid surface from the solution containing unreacted, soluble labeled antibody, and wherein in step (b) the labeled antibody is detected in either the solid phase or the separated solution.

32. A method for the detection of antigen contained in a biologically derived fluid sample, comprising the steps of:
(a) contacting said fluid sample with a diagnostic product of claim 1; said diagnostic product having the same antigenic determinants as said sample antigen; and
(b) detecting the sample antigen using a competitive assay.

33. The method of claim 32 in which in step (a) said diagnostic product is bound to a solid surface, and said sample also is contacted with soluble unlabeled complementary antibody, to cause competition binding for said complementary antibody between said diagnostic product and sample antigen, said method further comprising, prior to step (b), the steps of:
(c) separating the solid surface from the solution; and
(d) contacting the separated solid surface or solution with labeled anti-antibody capable of specifically binding said complementary antibody, and wherein in step (b) the labeled anti-antibody is detected.

34. The method of claim 32 in which said diagnostic product is labeled and in step (a) said sample is also contacted with immobilized complementary antibody to set up a competitive binding between the labeled diagnostic product and the sample antigen.

* * * * *